(12) United States Patent
Zhang et al.

(10) Patent No.: US 12,265,073 B2
(45) Date of Patent: Apr. 1, 2025

(54) METHOD AND SYSTEM FOR CHROMOGENIC ARRAY-BASED FOOD TESTING

(71) Applicants: University of Massachusetts, Boston, MA (US); The United States of America, as Represented by the Secretary of Agriculture, Washington, DC (US)

(72) Inventors: Boce Zhang, Dracut, MA (US); Hengyong Yu, Westford, MA (US); Yaguang Luo, Bethesda, MD (US); Xiaobo Liu, Dracut, MA (US)

(73) Assignee: University of Massachusetts, Boston, MA (US)

( * ) Notice: Subject to any disclaimer, the term of this patent is extended or adjusted under 35 U.S.C. 154(b) by 997 days.

(21) Appl. No.: 17/292,133

(22) PCT Filed: Nov. 5, 2019

(86) PCT No.: PCT/US2019/059816
§ 371 (c)(1),
(2) Date: May 7, 2021

(87) PCT Pub. No.: WO2020/097043
PCT Pub. Date: May 14, 2020

(65) Prior Publication Data
US 2021/0396730 A1   Dec. 23, 2021

Related U.S. Application Data

(60) Provisional application No. 62/757,388, filed on Nov. 8, 2018.

(51) Int. Cl.
*G01N 33/00* (2006.01)
*G01N 31/22* (2006.01)
(Continued)

(52) U.S. Cl.
CPC .............. *G01N 33/12* (2013.01); *G01N 31/22* (2013.01); *G01N 33/0047* (2013.01); *G01N 33/14* (2013.01); *G01N 33/583* (2013.01)

(58) Field of Classification Search
CPC ........................................................ G01N 33/12
(Continued)

(56) References Cited

U.S. PATENT DOCUMENTS 8,852,504 B2    10/2014   Suslick et al.
10,408,809 B1    9/2019   Emanuel et al.
(Continued)

FOREIGN PATENT DOCUMENTS

BR    102013019949 A2    3/2016
JP        3654956 B2     6/2005
(Continued)

OTHER PUBLICATIONS

Anonymous; "Manual for the laboratory identification and antimicrobial susceptibility testing of bacterial pathogens of public health concern in the developing world—Chapter 6"; World Health Organization, available online at https://www.who.int/csr/resources; Retrieved Jan. 7, 2020; pp. 62-102.
(Continued)

*Primary Examiner* — Christine T Mui
*Assistant Examiner* — Emily R. Berkeley
(74) *Attorney, Agent, or Firm* — Stites & Harbison, PLLC

(57) ABSTRACT

A chromogenic assay includes a substrate comprising an array of 5 or more dyes which react with volatile organic compounds, wherein the dyes are chromogenic when reacted with volatile organic chemical biomarkers, wherein the volatile organic chemical biomarkers comprise acids, alcohols, aldehydes, alkenes, amines, antioxidants, aromatic compounds, esters, ethylene, lactones, ketones, organosulfur compounds, sulfides, reactive oxygen species, terpenes, or a combination thereof. A method of detecting volatile organic chemical biomarkers includes contacting the chromogenic assay with a sample or sample headspace, wherein the sample or sample headspace is suspected of containing volatile organic chemical biomarkers, and identifying, based on a colorimetric pattern on the chromogenic assay after contacting, the source of the volatile organic chemical biomarkers. Also included are articles and systems including the chromogenic assay.

18 Claims, 9 Drawing Sheets

(51) Int. Cl.
*G01N 33/12* (2006.01)
*G01N 33/14* (2006.01)
*G01N 33/58* (2006.01)

(58) Field of Classification Search
USPC .......................................................... 436/20
See application file for complete search history.

(56) References Cited

U.S. PATENT DOCUMENTS

| | | |
|---|---|---|
| 2006/0223052 A1 | 10/2006 | MacDonald et al. |
| 2011/0046896 A1 | 2/2011 | Smajlovic |
| 2015/0094219 A1 | 4/2015 | Trowell et al. |

FOREIGN PATENT DOCUMENTS

| | | |
|---|---|---|
| KR | 20160011128 A | 1/2016 |
| WO | 2001062953 A2 | 8/2001 |
| WO | 2003039483 A2 | 5/2003 |
| WO | 2018148740 A1 | 8/2018 |

OTHER PUBLICATIONS

Ayob, M. et al.; "A rapid method for detection of Aldehyde-based flavour compounds in Polygonum minus cultured issue"; Malaysian Journal of Analytical Sciences, vol. 7, Issue No. 1; 2001; pp. 29-33.
International Search Report and Written Opinion for International Application PCT/US2019/059816; International Filing Date: Nov. 5, 2019; Date of Mailing: Feb. 3, 2020; 15 pages.
Kendall, H. et al.; "Food fraud and the perceived integrity of European food imports into China"; PLOS One, vol. 13, Issue No. 5; 2018; 27 pages; https://doi.org/10.1371/journal.pone.0195817.
Priye, A. et al.; "Colorimetric-Luminance Readout for Quantitative Analysis of Fluorescence Signals with a Smartphone CMOS Sensor"; Analytical Chemistry, vol. 90, Issue No. 21; 2018; pp. 12385-12389.
Wang, X. et al.; "Equipment-free chromatic determination of formaldehyde by utilizing pararosaniline-functionalized cellulose nanofibrous membranes"; Sensors and Actuators B: Chemical, vol. 203; 2014; pp. 333-339.

Fig. 3A-C

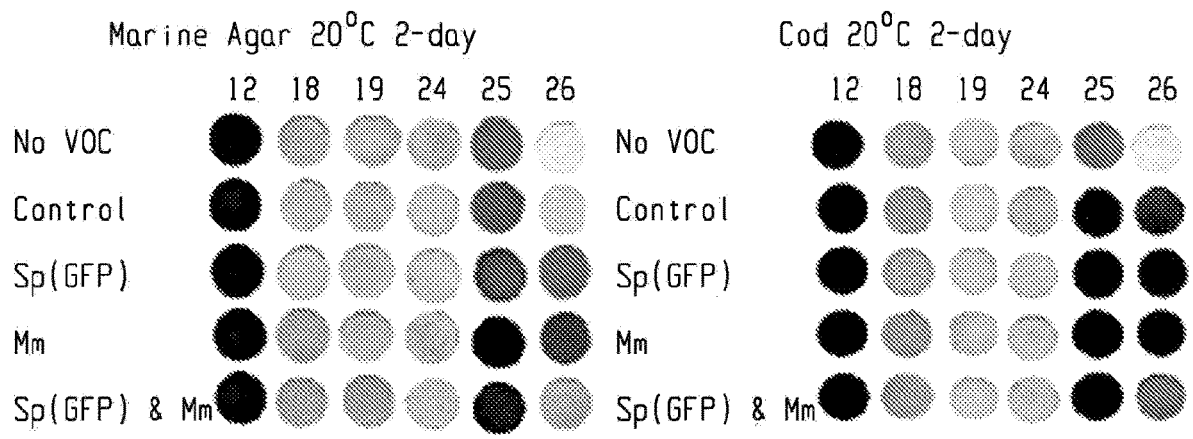
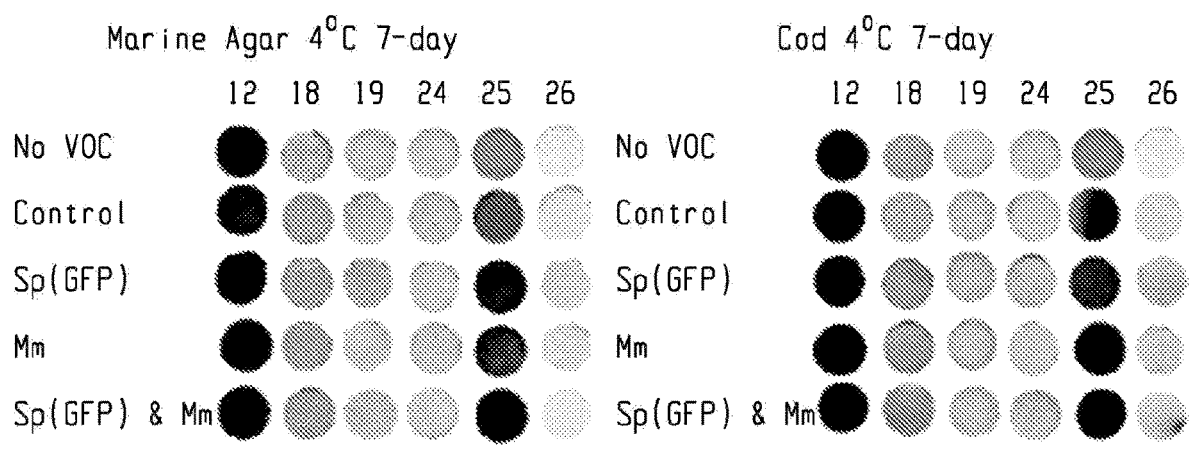
Fig. 9
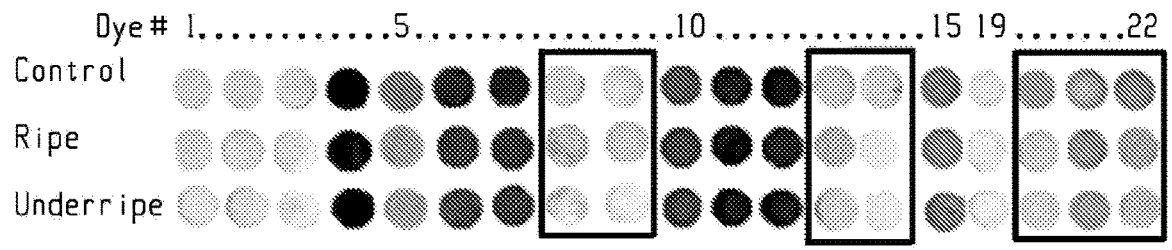
Fig. 10

METHOD AND SYSTEM FOR CHROMOGENIC ARRAY-BASED FOOD TESTING

CROSS REFERENCE TO RELATED APPLICATIONS

This application is a National Stage application of PCT/US2019/059816, filed Nov. 5, 2019, which claims the benefit of priority to U.S. Provisional Application No. 62/757,388, filed Nov. 8, 2018, both of which are incorporated by reference in their entirety herein.

BACKGROUND

Food security is of utmost importance to the U.S. and global economic stability and public health. Two primary threats pose a significant challenge to secure the food supply: food safety and post-harvest food waste. The two diverse problems, however, are plagued by one common contaminant—microorganisms. Foodborne illness outbreaks are major and on-going threats to global public health and the industry's economic wellbeing. According to Centers for Disease Control and Prevention (CDC), consumption of pathogen contaminated foods is responsible for 48 million illnesses including 125,000 hospitalizations and 3000 deaths per year in the US alone. *Salmonella* spp., *Clostridium perfringens*, *Campylobacter* spp. and *Escherichia coli* O157:H7 are the primary bacterial agents of concern, and food products with the presence of these pathogens must be destroyed, according to US Food and Drug Administration (FDA). The new FDA regulations under the Food Safety Modernization Act (FSMA) further require food processors to identify food safety hazards and develop preventive control to mitigate the risks. Thus, technologies that enable rapid and accurate detection and quantification of viable pathogens in food matrices are of critical needs and will serve as essential tools for the industry to identify the concerned products at early stages and remove them from commerce. Successful development and deployment of such technologies will lead to reduced food-borne illness outbreaks and costly recalls and market withdrawal.

Despite the recent advances in rapid detection platforms, very little success has been achieved to fulfill the needs for rapid quantification of viable pathogens in food. What is needed are compositions and methods for the multiplex quantification of viable pathogens in food.

In addition, in the United States, food waste is estimated at between 30-40 percent of the food supply. Approximately 69% of food loss occurs before entering the retail and consumer levels, corresponded to approximately 296 billion pounds and $358 billion worth of food in 2010. Spoilage of food can be triggered by multiple factors, including, but not limited to, natural physiological changes (e.g., ripening, aging, oxidizing, etc.), physiological defects and injures, variation in environmental factors (e.g., oxygen, temperature, and light, etc.), as well as the presence of microorganisms. There is an urgent demand to develop methods and systems that can monitor the overall condition of food.

BRIEF SUMMARY

In one aspect, a chromogenic assay comprises a substrate comprising an array of 5 or more dyes which react with volatile organic compounds, wherein the dyes are chromogenic when reacted with volatile organic chemical (VOC) biomarkers, wherein the VOC biomarkers comprise acids, alcohols, aldehydes, alkenes, amines, antioxidants, aromatic compounds, esters, ethylene, lactones, ketones, organosulfur compounds, sulfides, reactive oxygen species, terpenes, or a combination thereof.

In another aspect, a method of detecting VOC biomarkers comprises contacting the above-described chromogenic assay with a sample or sample headspace, wherein the sample or sample headspace is suspected of containing VOC biomarkers, and identifying, based on a colorimetric pattern on the chromogenic assay after contacting, the source of the VOC biomarkers.

An article includes the chromogenic assay described herein. In an aspect, the article further comprises color standards red, green, blue, and white that do not change color over time when exposed to VOCs.

In another aspect, a system comprises the chromogenic assay in operable communication with a machine learning database and algorithm.

BRIEF DESCRIPTION OF THE DRAWINGS

FIG. 5 bottom panel shows the *E. coli* (ATCC 8939) growth curve in BHI broth.

FIG. 6 bottom panel shows the *E. coli* (ATCC 8939) growth curve in BHI broth in at 4° C. and 37° C.

FIG. 9 shows multiplex identification of viable seafood spoilage causing bacteria *Shewanella putrefaciens* (Sp) and seafood pathogen *Morganella morganii* (Mm) in marine agar (MA) and cod in both refrigerating (4° C. for 7 days)

Figure 1:
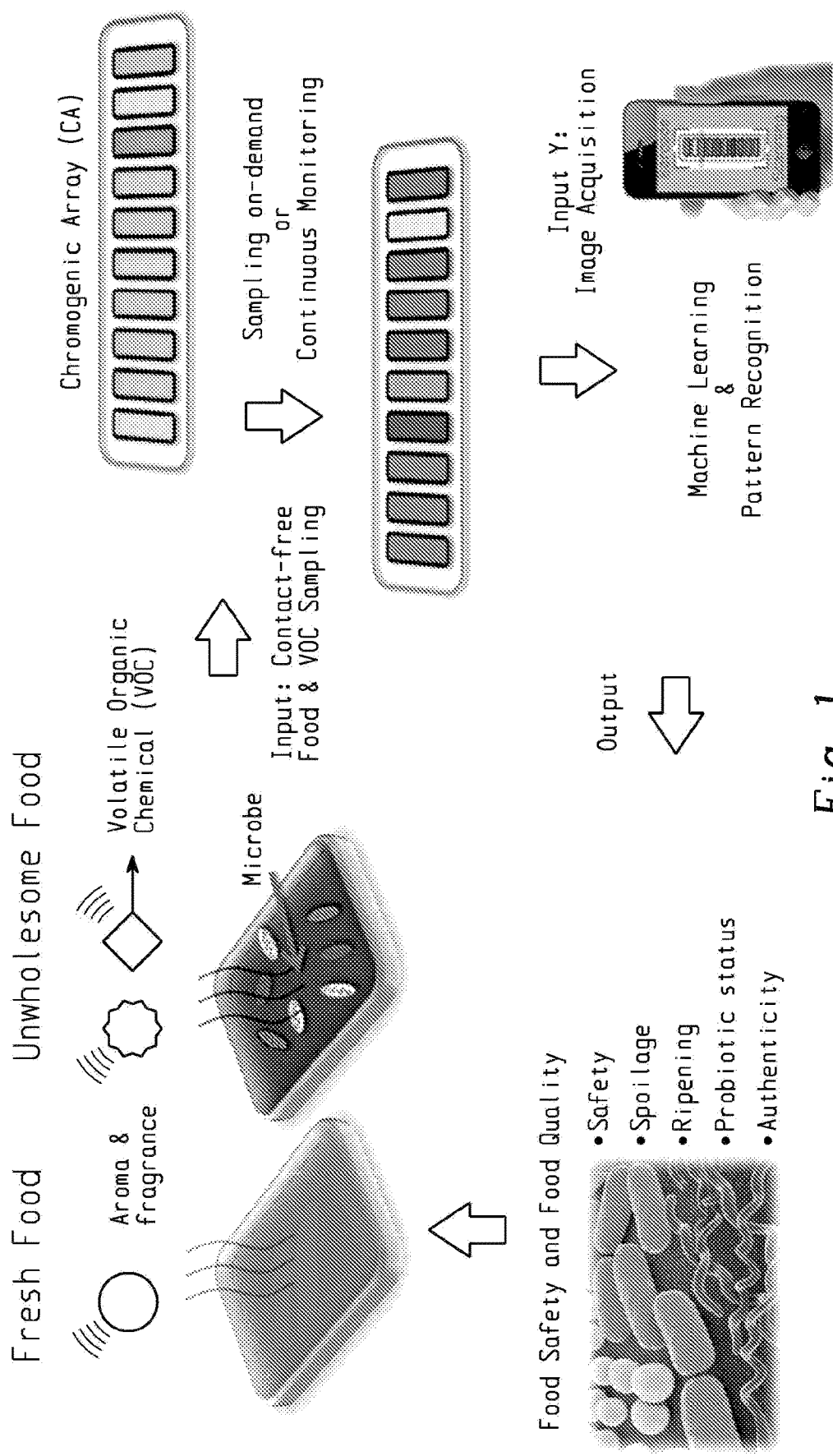
FIG. 1 shows an embodiment of a chromogenic assay (CA) coupled with machine learning and automated pattern recognition.

and temperature abuse scenarios (20° C. for 2 days). From top to bottom: Control (0-day), Control (agar or cod itself), Sp inoculated, Mm inoculated, cocktail Sp and Mm inoculated. These results suggest CA is capable of multiplex identification of both spoilage bacteria and pathogen in food matrices.

FIG. 10 shows CA monitoring of quality and physiological changes of climacteric produce (strawberry as the model). From top to bottom: control CA pattern without strawberry; CA pattern of ripened strawberry; CA pattern of underripe strawberry.

FIGS. 11a-d show machine learning of CA pattern using trained neural network (NN). Solid line indicates training accuracy using 75% of the CA replicates. Dashed line indicates test accuracy, which was validated using the remaining 25% of the PCA replicates that were unknown to the NN during training. 11a) Identification of microbial contaminant (CA data from single culture in BHI); 11b) Quantification of microbial contaminant (CA data from single culture in BHI); 11c) Detecting temperature abuse (CA data from single culture in BHI); 11d) Multiplex identification of microbial contaminants (CA data from both single and cocktail cultures in fresh-cut romaine lettuce).

The above-described and other features will be appreciated and understood by those skilled in the art from the following detailed description, drawings, and appended claims.

DETAILED DESCRIPTION

There are several issues in food safety that need to be addressed. i) Viability: Only viable microorganisms can cause microbial infection, toxin production, and food spoilage. The conventional quality assurance/quality control (QA/QC) testing still relies on the time-consuming plate counting methods. The more advanced rapid detection methods, however, have limited discriminative power to specifically identify viable bacteria. More importantly, none of these technologies are suitable for downstream non-destructive and continuous surveillance and monitoring. ii) Multiplex without customization: Each food commodity often faces multiple, and sometimes random, threats from dozens of major microbial contaminants. A monitoring and inspection system should entail capacities for multiplex detection. Nonetheless, conventional systems depend on recognition elements, like antibodies, enzymes, or even bacteriophages, which all require customization to achieve multiplex detection. However, customization can be self-prohibitory due to its economic feasibility. Therefore, a cost-effective and feasible approach is to develop a monitoring and inspection system that enables multiplex detection without the need to customize for individual biohazard. iii) Quantification: Microbial contaminants, especially pathogenic bacteria, vary significantly in their infectious dose. For instance, a *Shigella* infectious dose could be as low as 10 viable organisms in healthy adults, whereas, serotypes of *Listeria monocytogenes* would require $10^5$-$10^6$ viable organisms to develop listeriosis in a host. In addition, the microbial quantity in food constantly changes along the chain of distribution due to bacterial susceptibility to the changing environments, including, chemical stress, temperature, pH, water activity, ecological competition, and the like. Therefore, it is also critical to surveillance and monitor the microbial quantity, which can provide crucial information and implications to the development and implementation of risk-based preventive control from farm to fork.

Viable microorganisms produce genetic and metabolic biomarkers that are specific indicators to microbes, e.g., microbial identity, viability and environment. Described herein is a system and method for viable pathogen identification and/or quantification via the detection of those VOC biomarkers, specifically a chromogenic assay, also called a chromogenic array (CA) test strip. An embodiment of the system is shown in FIG. 1. The system can include machine learning and pattern recognition, which enables computer and cell phone-aided array or barcode reading to identify and quantify potential biohazards in food. These systems represent a significant breakthrough in the quantification of viable foodborne pathogens, and they are easily applicable and transferrable to many food safety and quality applications, including industrial quality assurance/quality control (QA/QC) toolkit, consumer point-of-care (POC), spoilage monitoring and food integrity.

One additional benefit of the assays and systems described herein is that VOCs can also be produced by plants as a biomarker for certain important quality criterion such as ripening or abnormal metabolism such as anaerobic metabolism.

Additionally, another benefit of the assays and systems described herein is that unique profiles of VOCs can also be produced by food that corresponds to natural physiological changes (e.g., ripening, aging, oxidizing, and the like), physiological defects and injures, and/orvariation in environmental factors (e.g., oxygen, temperature, and light, and the like).

In an aspect, a chromogenic assay comprises a substrate comprising an array of dyes, e.g., 2, 3, 4 or 5 or more dyes, which react with VOCs, wherein the dyes are chromogenic when reacted with VOC biomarkers. In an aspect, the selected dyes are optionally infused in porous absorbents. The optional porous absorbents have 1 to 100 nm pores, the structure of the porous absorbents provides active adsorption property, which can improve chromogenic reaction efficacy and reduce response time. The dyes are printed in an array on a substrate to create a CA. The integration of multiple dyes complement each other, and collectively, they possess unparalleled analytical power to differentiate viable pathogens. Preferably, the selected dyes cover all major volatile organic compound categories, and are chromogenic when reacting with microbial volatile organic compound biomarkers.

Exemplary substrates include paper, filter papers, plastics, glasses, metals, porous substrates, porous absorbents, or oxygen permeable membranes, air permeable membranes, and the like.

In an embodiment, a CA integrated with 7, 10, 15, 20, 23, or 30 or more dyes can produce unique arrays of color change after exposure to different biomarkers, such as biomarkers from microbes, fresh produce, climacteric produce, raw or processed meat, raw or processed poultry, raw or processed seafood, spices, dairy, grain, eggs, alcoholic or non-alcoholic beverages, or other processed and packaged food.

VOCs are produced by the metabolic reactions of microorganisms in food. These include such compounds as acids, alcohols, aldehydes, alkenes, amines, antioxidants, aromatic compounds, esters, ethylene, lactones, ketones, organosulfur and sulfide, reactive oxygen species, terpenes, and combinations thereof, that have been used as indicators for viable pathogen growth, and have been traditionally tested using heavily laboratory-relied analytical instruments, such as gas chromatography (GC) and high-performance liquid chromatography (HPLC). For instance, several aldehydes and ketones have been identified as fingerprint compounds to differentiate pathogenic *E. coli* O157:H7 from generic *E. coli* strains.

In an aspect, a CA comprises a substrate comprising an array of 5 or more dyes which react with VOCs, wherein the dyes are chromogenic when reacted with VOC biomarkers, wherein the volatile organic chemical biomarkers comprise acids, alcohols, aldehydes, alkenes, amines, antioxidants, aromatic compounds, esters, ethylene, lactones, ketones, organosulfur and sulfide, reactive oxygen species, terpenes, and combinations thereof.

In an embodiment, VOC biomarkers include all major volatile organic compound categories, including acids, alcohols, aldehydes, alkenes, amines, antioxidants, aromatic compounds, esters, ethylene, lactones, ketones, organosulfur and sulfide, reactive oxygen species, terpenes, and combinations thereof.

In an embodiment, the array of dyes provides an array of color change upon exposure to VOC biomarkers from viable pathogens, microorganisms, fresh produce, climacteric produce, raw or processed meat, raw or processed poultry, raw or processed seafood, spices, dairy, grain, eggs, alcoholic or non-alcoholic beverages, other processed and packaged food, or a combination thereof.

Table 1 provides a list of dyes that are chromogenic when reacted with the various VOCs.

TABLE 1

| Targeted VOC category | Dye selected |
|---|---|
| Acid | 1. Universal Indicator pH 2-10, from Ricca Chemical<br>2. 5% La(NO3)3 + 10% Iodine + 0.5M Ammonia<br>3. All pH indicators |
| Alcohol | 1. VP reagent: 5% alpha-naphthol: 40% KOH = 3:1, v/v<br>2. Westerfield test: 0.5% creatine: 2.5N alkaline a-naphthol (1.0 g of a-naphthol per 20 ml of 2.5N NaOH) = 1:1, v/v.<br>3. Potassium dichromate + Sulfuric acid + 1,5-Diphenylcarbazide<br>4. 0.1M H5IO5 + 4% (w/v) CuSO4 + ethylene glycol + 1.5% (w/v) p-hydroxydiphenyl + 0.5% (w/v) NaOH |
| Aldehyde | 1. 2,4-Dinitrophenylhydrazine + H2SO4<br>2. 2,4-Dinitrophenylhydrazine + p-Toluenesulfonic acid (TSOH)<br>3. 4,4'-azodianiline + H2SO4<br>4. 4,4'-azodianiline + TSOH<br>5. Pararosaniline chloride + H2SO4<br>6. Pararosaniline + TSOH<br>7. Tollen's reagent<br>8. Benedict reagent<br>9. Bromophenol blue + Tetrabutylammonium hydroxide (TBAH)<br>10. Nitrazine yellow + TBAH<br>11. Chlorophenol Red + TBAH<br>12. Zn(NO3)2 + Bromophenol blue<br>13. 20% Sodium nitroprusside + 30% NaOH + glacial acetic acid |
| Alkene | 1. Gold (III) chloride + cyclic urea<br>2. Peroxynitric acid<br>3. Universal Indicator pH 2-10, from Ricca Chemical<br>4. All pH indicators |
| Amine | 5. Zinc (II) meso-Tetraphenylporphine,<br>6. Meso-Tetraphenylporphyrin<br>7. Ni(II) tetraphenylporphyrin<br>8. Vanadyl tetraphenylporphine<br>9. Fe(III) tetraphenylporphyrin<br>10. Cobalt(II) tetraphenylporphyrin<br>11. Mg(II) tetraphenylporphyrin<br>12. Mn(III) tetraphenylporphyrin<br>13. Cr(III) tetraphenylporphyrin<br>14. Pt(II) tetraphenylporphyrin<br>15. Folin's reagent (sodium 1,2-naphthoquinone-4-sulfonate)<br>16. 5% sodium nitroprusside + 10% acetaldehyde + 2% sodium carbonate, (CAS: 497-19-8)<br>17. Thiodiphenylamine (Phenothiazine) + methanolic solution of bromine |
| Antioxidants and/or reactive oxygen species (ROS)* | 1. 1,3,3-Trimethyl-2-[3,7,12,16-tetramethyl-18-(2,6,6-trimethylcyclohex-1-en-1-yl)octadeca-1,3,5,7,9,11,13,15,17-nonaen-1-yl] cyclohex-1-ene (beta-carotene)<br>2. 2,2'-Azinobis(3-ethylbenzothiazoline)-6-sulfonic acid (ABTS)<br>3. 2,2-Diphenyl-1-picrylhydrazyl (DPPH)<br>4. Ferric tripyridyltriazine (FeIII-TPTZ) complex<br>5. Polyphenol oxidase<br>6. Fluorescent compounds |

TABLE 1-continued

| Targeted VOC category | Dye selected |
|---|---|
| Aromatic (including Indole) | 1. Kovac's reagent, Remel<br>2. 3-Methyl-2-benzothiazolone hydrazine and ferric chloride in aqueous methanol<br>3. Chitosan-capped silver nanoparticles<br>4. p-Sulfonatocalix[6]arene-modified gold nanoparticles<br>5. Squaraine derivatives<br>6. Tetrabutylammonium hydroxide |
| Ester | 1. Ferric ammonium sulfate + 1,10-phenanthroline for Autoinducer-2<br>2. Hydroxylamine hydrochloride + sodium hydroxide + ferric chloride + 2,4-Dinitrophenol |
| Ethylene | 1. $KMnO_4$<br>2. Molybdenum blue<br>3. Palladous sulfate ($PdSO_4$) + ammonium molybdate<br>4. Silicomolybdate protocol ($NaSiF_6$) + ammonium molybdate |
| Lactone | 1. Beta-galactosidase + Beta-Glo ®(6-O-β-galactopyranosyl-luciferin, Promega) or β-galactosidase + X-Gal (5-bromo-4-chloro-3-indolyl-β-D-galactopyranoside), for N-acyl homoserine lactone (AHL)<br>2. Hydroxylamine hydrochloride + sodium hydroxide + ferric chloride + 2,4-Dinitrophenol<br>3. Kedde's reagents |
| Ketone | 1. 2,4-Dinitrophenylhydrazine + $H_2SO_4$<br>2. 2,4-Dinitrophenylhydrazine + p-Toluenesulfonic acid (TSOH)<br>3. 4,4'-azodianiline + $H_2SO_4$<br>4. 4,4'-azodianiline + TSOH<br>5. Pararosaniline chloride + $H_2SO_4$<br>6. Pararosaniline + TSOH<br>7. Tollen's reagent<br>8. Benedict reagent<br>9. Bromophenol blue + Tetrabutylammonium hydroxide (TBAH)<br>10. Nitrazine yellow + TBAH<br>11. Chlorophenol Red + TBAH<br>12. $Zn(NO_3)_2$ + Bromophenol blue<br>13. 20% Sodium nitroprusside + 30% NaOH + glacial acetic acid |
| Organosulfur and sulfide | 1. $CuCl_2$ + $NH_4Cl$ + concentrated ammonia + Hydroxylamine hydrochloride<br>2. Magnesium salt or nanoparticle<br>3. Calcium salt or nanoparticle<br>4. Silver salt or nanoparticle<br>5. Zinc salt or nanoparticle<br>6. Gold salt or nanoparticle<br>7. Chloranil |
| Terpene | 1. Vanillin-glacial acetic acid + perchloric acid<br>2. Liebermann-Burchard test |

\* Antioxidant includes carotenoids, essential oils, flavonoids, polyphenols, vitamin, etc. Reactive oxygen species include $H_2O_2$, superoxide, singlet oxygen, hydroxyl/peroxyl/alkoxyl free radicles, oxides of nitrogen, ozone, hypochlorous acid, etc.

Table 2 provides a list of chromogenic dyes that are presented in the figures (FIG. 2, FIGS. 3A-C, FIG. 4, FIG. 5, FIG. 6, FIG. 8, FIG. 9, and FIG. 10).

TABLE 2

List of chromogenic dyes used

| Dye No. | Chemical Compositions |
|---|---|
| 1 | 2,4-Dinitrophenylhydrazine + Sulfuric acid |
| 2 | 2,4-Dinitrophenylhydrazine + p-Toluenesulfonic acid |
| 3 | 4,4'-Azodianiline + Sulfuric acid |
| 4 | 4,4'-Azodianiline + p-Toluenesulfonic acid |
| 5 | 4,4'-Azodianiline + p-Toluenesulfonic acid |
| 6 | Pararosaniline + Sulfuric acid |
| 7 | Pararosaniline + p-Toluenesulfonic acid |
| 8 | Tollen's Reagent |
| 9 | Benedict's Reagent |
| 10 | Bromophenol blue + Tetrabutylammonium hydroxide |
| 11 | Nitrazine yellow + Tetrabutylammonium hydroxide |
| 12 | Chlorophenol red + Tetrabutylammonium hydroxide |
| 13 | Zinc nitrate + Bromophenol blue |
| 14 | Sodium nitroprusside + Sodium hydroxide + Glacial acetic acid |
| 15 | Lanthanum (III) nitrate hexahydrate + Iodine + Ammonia |
| 16 | Kovac's reagent |
| 17 | Copper chloride + Ammonium chloride + Ammonia + Hydroxylamine hydrochloride |
| 18 | Silver nitrate |
| 19 | Voges-Proskauer's reagent |
| 20 | Zinc tetraphenylporphyrin |
| 21 | Sodium nitroprusside + Acetaldehyde + Sodium carbonate |
| 22 | Thiodiphenylamine + bromine |
| 23 | Universal pH indicator |

TABLE 2-continued

List of chromogenic dyes used

| Dye No. | Chemical Compositions |
|---|---|
| 24 | Cobalt tetraphenylporphyrin |
| 25 | Bromocresol purple |
| 26 | Silver nitrate in an aqueous nitric acid solution |

For example, amine-containing organic dyes provide chromogenic reactions with aldehyde and ketone volatile organic compounds. Specifically, 2,4-dinitrophenylhydrazine (phenylhydrazine), 4,4'-azodianiline (dianiline) and pararosaniline (fuchsine), bromophenol blue, nitrazine yellow, chlorophenol red are the organic dyes used to provide chromogenic reactions with aldehyde and ketone metabolites. Tollen's reagent, Benedict's reagent, zinc nitrate, sodium nitroprusside help to cover all major VOC categories.

Advantageously, while some of the dyes can be toxic, the CA only reacts with VOCs(FIG. 1), so it does not require any direct contact with the food itself.

To fabricate the CA, the dyes can be infused in porous adsorbents prior to application to the substrate to provide so-called nano-dyes, which provide active absorption of VOC molecules, and promote chromogenic reaction efficiency and reduce reaction time. Porous absorbents are selected due to properties such as high surface area, surface reactivity, structural stability, and regular channel-type structures, which are useful for active absorption properties. Exemplary porous absorbents include MCM-41, a nanoporous silica nanobead which has been used as an efficient adsorbent to promote active adsorption of volatile organic compound. Active adsorption enabled by porous absorbents significantly increases the reaction rate between the volatile organic compound biomarker and the infused dyes. Porous absorbents can be infused with dyes by mixing the dye solution with porous absorbents for overnight at room temperature. Purified nano-dyes can then be obtained after washing via centrifugation in corresponding organic solvent. Other alternatives for porous absorbents include butyl acrylate polymer nanoparticles and anion exchange beads.

The fabrication of the CA can be done by drop casting, pipette spotting, airbrushing, printing, screen printing, ink-jet printing, contact imprinting, microarray dispensing, or nanoscale dispensing dye solution on the precut strip. The strips with the dye mixtures are then dried under vacuum.

In an aspect, the assay can detect viable microoganisms at a concentration as low as 10-10,000 and as high as 1,000,000-1,000,000,000 colony forming unit per milliliter or per gram.

In an aspect, a method of detecting VOC biomarkers, comprises contacting the chromogenic assay described herein with a sample or sample headspace, wherein the sample or sample headspace is suspected of containing VOC biomarkers, and identifying, based on a colorimetric pattern on the chromogenic assay after contacting, the source of the VOC biomarkers. Contacting may be continuous, or for a period of time such as 15 minutes to 2 hours, 15 minutes to 24 hours, 15 minutes to 48 hours, 15 minutes to 7 days, 15 minutes to 1 months, 15 minutes to 1 year, or 15 minutes to 5 years. The CA assay may be an on-demand sampling assay.

For example, to use the CA, sample solution was dropped on the test strips and reacted for 15 min before the colors of the control and sample test strips were recorded. For extremely volatile target analytes, such as thiol compounds, hydrogen sulfide and ethanol, strips were exposed to vapor of target analytes for 30 min.

Exemplary samples include a food sample, and the source of the VOC biomarkers may be identified as a microorganism. Exemplary microorganisms comprise pathogens like *Aspergillus* spp., *Bacillus* spp., *Brucella* spp., *Campylobacter* spp., *Clostridium* spp., *Cronobacter sakazaki*, *Cryptosporidium* spp., *Cyclospora cayetanensis*, *Giardia intestinalis*, *Listeria monocytogenes*, *Morganella morganii*, *Mycobacterium bovis*, pathogenic *E. coli* spp., *Salmonella* spp. (*S. enterica* serotype *Typhi* and non-typhoidal), *Shigella* spp., *Staphylococcus aureus*, *Streptococcus* spp., *Trichinella* spp., *Toxoplasma gondii*, *Vibrio* spp., *Yersinia* spp.; spoilage causing microbes like *Acetobacter* spp., *Acinetobacter* spp., *Aeromonas* spp., *Bacillus* spp., *Botrytis cinerea*, *Brochothrix* spp., *Candida* spp., *Carnobacterium* spp., *Cladosporium* spp., *Claviceps* spp., *Enterobacter* spp., *Enterococcus* spp., *Erwinia carotovora*, *Fusarium* spp., generic *E. coli* spp., *Geotrichum* spp., *Gluconobacter* spp., *Klebsiella* spp., *Lactobacillus* spp., *Leuconostoc* spp. *Moraxella* spp., *Mucor* spp., *Pediococcus* spp., *Penicillium* spp., *Photobacterium* spp., *Proteus* spp., *Pseudomonas* spp., *Psychrobacter* spp., *Rhizopus* spp., *Saccharomyces* spp., *Serratia* spp., *Shewanella* spp., *Sportrichum* spp., *Yersinia* spp.; Probiotic and fermentation microbes like *Acetobacter* spp., *Bifidobacterium* spp., *Candida* spp., *Enterococcus* spp., *Geotrichum* spp., *Gluconobacter* spp., lactic-acid bacteria (LAB), *Lactobacillus* spp., *Lactococcus* spp., *Leuconostoc* spp., *Oenococcus* spp., *Pediococcus* spp., *Penicillium* spp., *Propionibacterium* spp., *Saccharomyces* spp., *Streptococcus* spp., *Weissella* spp.; or a combination comprising one or more of the foregoing. In an aspect, the method can comprise pre-harvest monitoring of diseases and/or the presence of pathogens on edible plants, livestock animals, or poultry.

Exemplary samples include a food sample suspected of temperature abuse, and the source of the VOC biomarkers is identified as physiological damage or a microorganism, such as a spoiling-causing microorganism or a food pathogen. Exemplary microorganisms comprise pathogens like *Aspergillus* spp., *Bacillus* spp., *Brucella* spp., *Campylobacter* spp., *Clostridium* spp., *Cronobacter sakazaki*, *Cryptosporidium* spp., *Cyclospora cayetanensis*, *Giardia intestinalis*, *Listeria monocytogenes*, *Morganella morganii*, *Mycobacterium bovis*, pathogenic *E. coli* spp., *Salmonella* spp. (*S. enterica* serotype *Typhi* and non-typhoidal), *Shigella* spp., *Staphylococcus aureus*, *Streptococcus* spp., *Trichinella* spp., *Toxoplasma gondii*, *Vibrio* spp., *Yersinia* spp.; spoilage causing microbes like *Acetobacter* spp., *Acinetobacter* spp., *Aeromonas* spp., *Bacillus* spp., *Botrytis cinerea*, *Brochothrix* spp., *Candida* spp., *Carnobacterium* spp., *Cladosporium* spp., *Claviceps* spp., *Enterobacter* spp., *Enterococcus* spp., *Envinia carotovora*, *Fusarium* spp., generic *E. coli* spp., *Geotrichum* spp., *Gluconobacter* spp., *Klebsiella* spp., *Lactobacillus* spp., *Leuconostoc* spp. *Moraxella* spp., *Mucor* spp., *Pediococcus* spp., *Penicillium* spp., *Photobacterium* spp., *Proteus* spp., *Pseudomonas* spp., *Psychrobacter* spp., *Rhizopus* spp., *Saccharomyces* spp., *Serratia* spp., *Shewanella* spp., *Sportrichum* spp., *Yersinia* spp.; Probiotic and fermentation microbes like *Acetobacter* spp., *Bifidobacterium* spp., *Candida* spp., *Enterococcus* spp., *Geotrichum* spp., *Gluconobacter* spp., lactic-acid bacteria (LAB), *Lactobacillus* spp., *Lactococcus* spp., *Leuconostoc* spp., *Oenococcus* spp., *Pediococcus* spp., *Penicillium* spp., *Propionibacterium* spp., *Saccharomyces* spp., *Streptococcus* spp., *Weissella* spp.; or a combination comprising one or more of the foregoing.

Exemplary samples also include a fresh food sample and the source of the VOC biomarkers is the species, genetic traits, physiological state, abnormal metabolism, or ripeness of the food sample.

The methods can include continuous monitoring of sample status, differentiation of temperature, or determination of temperature abuse history.

The methods can include continuous monitoring of probiotic status of fermented food selected from yogurt, sauerkraut, kimchi, kefir, miso, tempeh, buttermilk, chocolate, cheese, cider, pickle, sourdough.

The methods can include postharvest monitoring of perishable food in climate-controlled shipping containers and storage facility, as well as plastic container, trays, modified atmosphere packaging, controlled atmosphere packaging, cartons, paper bags, and micro-perforated plastic bags, and the like.

The method can include preharvest monitoring of diseases and presence of pathogens on edible plants and livestock animals, poultry, as well as environmental monitoring of greenhouses and animal husbandry.

In an aspect, the method comprises authenticity verification of a fermented and/or aged food or beverage selected chocolate, cheese, balsamic vinegar, beer, and wine.

Exemplary food samples include fresh produce, climacteric produce, raw or processed meat, raw or processed poultry, raw or processed seafood, spices, dairy, grain, eggs, alcoholic or non-alcoholic beverages, or other processed and packaged food.

The methods can include the method comprises pathogen monitoring, probiotic monitoring, authenticity test, risk assessment, smart packaging, QA/QC, and consumer POC testing.

Upon the successful fabrication of the CAs, microbial cultures were used to calibrate and establish database for the identification and quantification of multiple viable microbes. *E. coli* O157:H7 (ATCC 43895) and generic *E. coli* (ATCC 8739) were compared to demonstrate the discriminatory power of the array test strip between pathogens and the microflora. Additional major foodborne pathogens can used to establish the database, including *Salmonella* spp., *V. parahaemolyticus, B. cereus, S. aureus*, enterotoxin and diarrheagenic *E. coli*, Shiga toxin-producing *E. coli* O157:H7, *Listeria monocytogenes, Clostridium* spp., *Campylobacter* spp., and *Cronobacter sakazaki*. Currently, existing methods, e.g., U.S. Pat. No. 8,852,504, describe a system that adopts dyes to identify microorganisms. However, the existing methods have significant limitation when applied to food. The existing methods were solely based on the VOCs produced by microbes to achieve identification and quantification. However, in real food, the background of VOCs constantly changes due to natural physiological changes (e.g., ripening, aging, oxidizing, etc.), physiological defects and injuries, variation in environmental factors (e.g., oxygen, temperature, light, and the like) without the presence of an microorganisms. The natural shifting background generates huge errors and significantly impairs the reliability and accuracy of the existing methods. Thus, an overall survey and monitoring system is very much needed by the food industry to produce accurate and reliable results that cover natural physiological changes (e.g., ripening, aging, oxidizing, and the like), physiological defects and injuries, variation in environmental factors (e.g., oxygen, temperature, light, and the like) as well as the presence of microorganisms in food.

Thus, an overall survey and monitoring system is very much needed by the food industry to produce accurate and reliable results that covers natural physiological changes (e.g., ripening, aging, oxidizing and the like), physiological defects and injuries, variation in environmental factors (e.g., oxygen, temperature, light, and the like), as well as the presence of microorganism in food. In addition to microbial detection and quantification, VOCs are important biomarkers for fresh fruits and vegetables in differentiating certain species or genetic traits, and fruit ripening stages that are critical for harvesting or processing related decision making, and the like. Currently, there are a number of commercial products such as electronic-nose and intelligent sensor labels (e.g. commercially available under the tradename ripesSense®) that have been developed to suite these needs. While these products are based on VOC biomarker principles, they are either too expensive and not user-friendly (E-nose) or not versatile enough for a broad application (ripeSense®). More importantly, these methods are significantly limited to measure one variable at a time, and cannot monitor complex and multiplex changes involved in spoilage, pathogens, and ripening, simultaneously. However, these complex changes and multiplex signals are natural and very common in food products. Thus, existing products and technologies are greatly limited in real-world samples, and a versatile, inexpensive, and user friendly technology targeting the overall VOC profile is very much needed by the food industry. Specifically, the strips comprising integrated arrays of dyes developed for the pathogen detection can be tailored to respond to the volatile organic compounds from the food matrices and the microorganisms.

In addition to visual signs, the color changes on the chromogenic array can be digitized through image processing and pattern recognition. A multilayer neural network, or similar algorithm can be developed, and the strips linked with smartphone technology. These artificial intelligence (AI) enabled sensors will allow users to conveniently, inexpensively, and accurately detect and quantify volatile organic compound biomarkers. The products or applications may include detection device for human pathogens or spoilage microbes, intelligent packages with color change stickers/labels to indicate optimum ripening stage for consumption, smart supply chain management and inventory based on product quality to minimize food loss and wastes, determining authenticity and/or probiotic status of fermented, or direct application of stickers on fruits in the field to guide best harvesting time decision making.

Also included herein are articles comprising the CA, such a sticker, a label, a standalone strip, a package, or a container. The article can further comprise color standards red, green, blue, and white that do not change color over time when exposed to VOC. The color standards can eliminate the requirement to control lighting conditions and camera settings when taking images, and allows standardization and correction of the color pattern in any lighting conditions and camera settings.

A system comprises the chromogenic assay described herein in operable communication with a machine learning database and algorithm. The machine learning database and algorithm can comprise data for multiplex identification and quantification of microbes, the physiological status of the sample, injuries and diseases, temperature abuse, or a combination comprising at least one of the foregoing. The machine learning database can comprise a neural network comprising a plurality of triplets in color space, such as RGB or LAB values. The system can further comprise a smartphone, for example. The smartphone may comprise the machine learning database and algorithm.

In an aspect, machine learning techniques are used to automatically segment the dye array images and extract the corresponding color information, such as RGB or LAB values.

The machine learning techniques may include a conventional neural network, a fully convolutional network, feature pyramid network, generative adversarial network, deep convolutional network, and DeepLab. DeepLab is a Semantic Image Segmentation method that include Deep Convolutional Nets, Atrous Convolution, and Fully-Connected Conditional Random Fields.

The invention is further illustrated by the following non-limiting examples.

EXAMPLES

Example 1: Exemplary Design of an Array Test Strip

FIG. 1 illustrates an embodiment of a CA test strip. Briefly, viable pathogens produce volatile organic compounds in the headspace, as well as soluble metabolites in a food matrix during microbial metabolism. An array of integrated dyes, printed on a test strip, reacts with the target volatile organic compounds and metabolites. A short (15 minutes) direct sampling of the food or headspace will render color changes of the array dyes. An integration of 20 or more dyes will appear as arrays, which maximize the ability to differentiate a large variety of volatile organic compounds from foodborne pathogens. A machine learning algorithm adopted as a computer or cell phone-aided pattern recognition can extract information regarding pathogen identity and quantity. In addition, each CA has built-in color standard in red, green, blue, and white, that do not change color over time and when exposed to VOC. The color standards serve as a correction and standardization of the CA pattern image when taken at different lighting conditions and camera settings.

Specifically, 2,4-dinitrophenylhydrazine (phenylhydrazine), 4,4'-azodianiline (dianiline) and pararosaniline (fuchsine), bromophenol blue, nitrazine yellow, chlorophenol red are the organic dyes used for the aldehyde and ketone metabolites. Tollen's reagent, Benedict's reagent, zinc nitrate, sodium nitroprusside are also integrated in the dye array to achieve maximum differentiation ability.

The matrix used for the test strip was P5 filter purchased from Fisher Scientific. To prepare the CA, dyes, including metalloporphyrins, 2,4-dinitrophenylhydrazine, 4,4'-azodianiline pararosaniline chloride, bromophenol blue, nitrazine yellow, chlorophenol red and Kovacs reagent, as well as inorganic dyes, such as Tollen's reagent, Benedict's reagent, zinc nitrate, sodium nitroprusside, silver nitrate and iodine were used. The organic nano-dyes were dissolved in 2-Methoxyethanol (Acros) or DI water and mixed with predetermined appropriate volume of 1 M sulfuric acid (Millipore), p-toluenesulfonic acid (TSOH) (Acros) or tetrabutylammonium hydroxide (TBAH) (Acros). Inorganic nano-dyes were dissolved in DI water with predetermined acidic or basic condition as a favorable condition for the reaction with microbial volatile organic compounds. The commercial reagents, such as Tollen's reagent, Benedict's reagent and Kovacs reagent were used as received. The fabrication of the CA test strips was done by drop casting 10 µL of the dye solution on the pre-cut strip from the substrate (15 mm×4 mm). The strips with the dye mixtures were dried under vacuum for 15 min and ready for use. To test the functionality of the CA, 50% glutaraldehyde solution (Fisher Chemical) were used as the representative aldehyde compound. 2-Nonanone (Acros) were used as the representative ketone compound, as well as the fingerprint metabolite for $E.\ coli$ O157:H7. 10 µL of sample solution was dropped on the test strips and reacted for 15 min before the colors of the control and sample test strips were recorded. For extremely volatile target analytes, such as 1-butanothiol (a representative thiol compound), hydrogen sulfide and ethanol, strips were exposed to vapor of target analytes for 30 min. Upon the successful validation of all colorimetric assays, dyes were selected for the assembly of CA. Strips with the selected dyes were dried and taped on double side tapes with the other side of the tape stick on a piece of plastic film. A pool of 23 dyes was selected and were used for the preliminary test.

Figure 2:
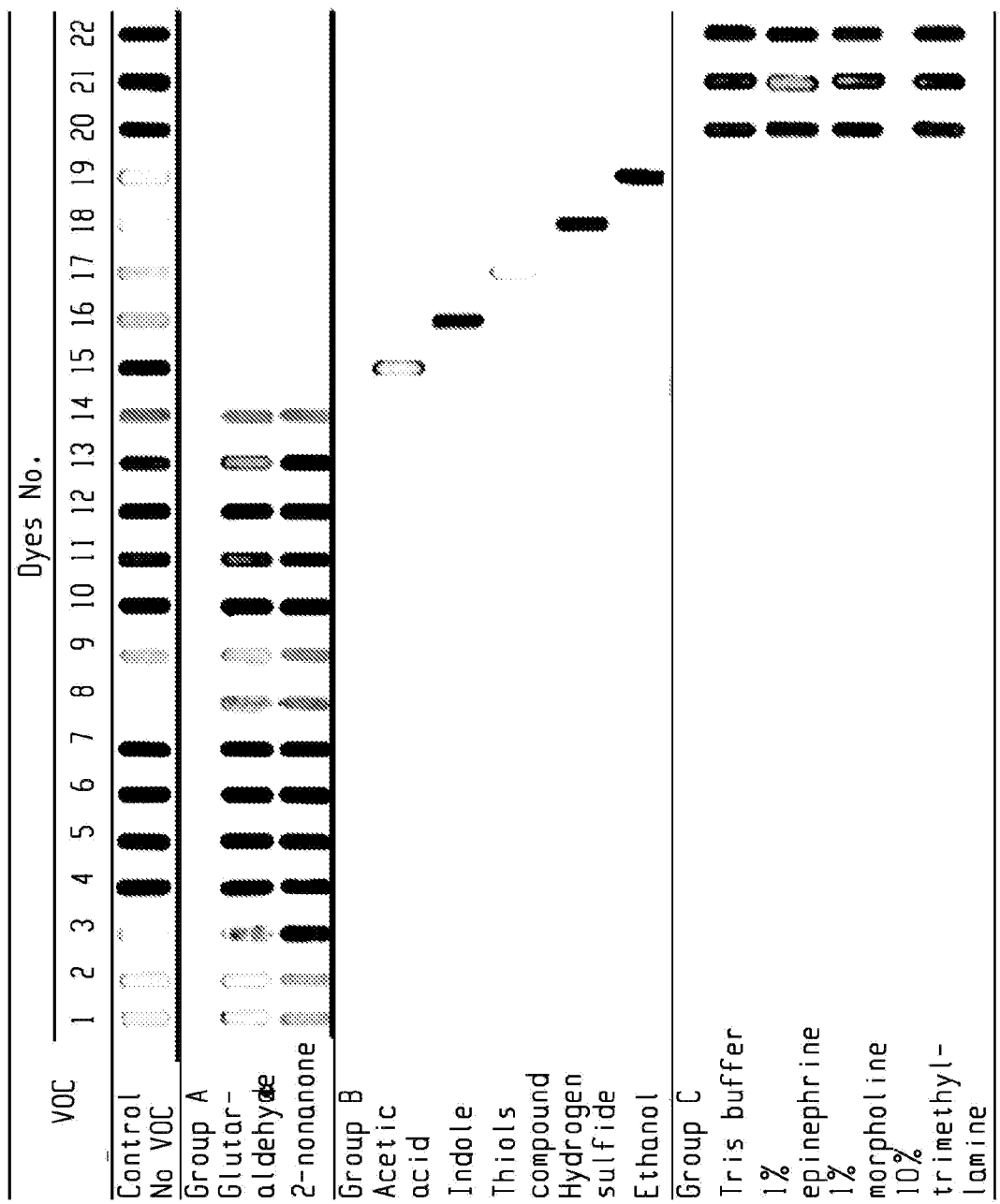
FIG. 2 shows CA dye selection that covers a broad range of VOC categories, including: Group A—aldehydes, ketones; Group B: acids, aromatic compounds, sulfur compounds, alcohols; Group C: Amines. Dye numbers (#1 to #22) are provided below.

As proof-of-concept, the color change pattern of several selected CA is presented in FIG. 2. In FIG. 2, glutaraldehyde (representative acetaldehyde) and 2-nonanone (representative ketone and fingerprint metabolites of $E.\ coli$ O157: H7) were used to demonstrate the response of the CA test strips to viable pathogen metabolites. FIG. 2 showed that amine-containing dyes (2,4-dinitrophenylhydrazine, 4,4'-azodianiline and pararosaniline) provided very distinct color changes upon addition of aldehyde and ketones. The color change is due to nucleophilic addition of carbonyl group by an amine in the formation of an imine, which gives a difference UV-vis absorption band. The addition of aldehyde reduced silver ions in Tollen's reagent and copper ions in Benedict's reagent on a test strip. Indole also formed a red complex with p-dimethylaminobenzaldehyde in Kovac's reagent drop cast on a test strip.

Furthermore, to demonstrate the feasibility of the chromogenic assay pool for viable pathogen metabolomics biomarkers detection, various microbial metabolomics biomarkers, including acetic acid, indole (distinct metabolites for $E.\ coli$), thiols compounds, hydrogen sulfide and ethanol, and their chromogenic assay color change pattern is presented in FIG. 2. For amine metabolomics biomarkers, which are vital indicators for food safety, especially for meat and seafood, several chromogenic assays and the color change pattern for primary, secondary and tertiary amine are showed in FIG. 2. Distinctive color changes are observed after these chromogenic assays were exposed to corresponding target analytes. The color changes observed from the strips showed good reproducibility, as the three independent trails showed similar color changes for each test.

Table 3 provides an example of color description and RGB values of the CA patterns presented in FIG. 2. FIGS. 3A-C, FIG. 4, FIG. 5, FIG. 6, FIG. 8, FIG. 9, and FIG. 10 have similar color change, but only presented in black/white.

TABLE 3

Color description and RGB values of the CA patterns presented in FIG. 2.

| VOC | Dyes No. (D#) | | | | |
|---|---|---|---|---|---|
| Control | D#1 | D#2 | D#3 | D#4 | D#5 |
| No VOC | Yellow | Yellow | Cream | Dijon | Purple |
| | 255, 255, 167 | 255, 255, 186 | 254, 255, 241 | 129, 127, 49 | 178, 104, 129 |
| | D#6 | D#7 | D#8 | D#9 | D#10 |
| | Violet | Pale Violet | White | Sky Blue | Blue |
| | 102, 6, 4 | 103, 4, 55 | 255, 255, 255 | 198, 251, 255 | 16, 67, 216 |
| | D#11 | D#12 | D#13 | D#14 | D#15 |

TABLE 3-continued

Color description and RGB values of the CA patterns presented in FIG. 2.

| VOC | Dyes No. (D#) | | | | |
|---|---|---|---|---|---|
| | Azure<br>130, 199, 231<br>D#16<br>Cream<br>247, 237, 202<br>D#21<br>Dark Pink<br>207, 151, 158 | Dark Violet<br>52, 26, 122<br>D#17<br>Sky Blue<br>218, 249, 277<br>D#22<br>Pink<br>252, 133, 135 | Gold<br>219, 173, 51<br>D#18<br>Pale Cream<br>254, 254, 252 | Pink<br>235, 202, 159<br>D#19<br>Pale Yellow<br>251, 250, 233 | Brown<br>190, 112, 24<br>D#20<br>Pale Brown<br>191, 170, 137 |
| | | | Group A | | |
| Glutaralderhyde | D#1<br>Pale Yellow<br>255, 252, 199<br>D#6<br>Violet<br>10, 17, 151<br>D#11<br>Azure<br>148, 207, 244 | D#2<br>Pale Yellow<br>255, 255, 179<br>D#7<br>Violet<br>23, 8, 138<br>D#12<br>Violet<br>85, 52, 143 | D#3<br>Pale Yellow<br>245, 218, 149<br>D#8<br>Pale pink<br>245, 217, 194<br>D#13<br>Yellow<br>253, 233, 101 | D#4<br>Orange<br>249, 125, 20<br>D#9<br>Sky Blue<br>200, 249, 252<br>D#14<br>Pale Pink<br>235, 218, 188 | D#5<br>Black<br>17, 6, 14<br>D#10<br>Blue<br>19, 64, 220 |
| 2-Nona<br>None | D#1<br>Yellow<br>248, 246, 132<br>D#6<br>Dark Red<br>132, 2, 49<br>D#11<br>Dark Azure<br>43, 133, 194 | D#2<br>Yellow<br>248, 243, 118<br>D#7<br>Dark Purple<br>157, 2, 73<br>D#12<br>Navy<br>15, 2, 71 | D#3<br>Red<br>225, 104, 5<br>D#8<br>Pink<br>240, 214, 177<br>D#13<br>Green<br>19, 76, 69 | D#4<br>Orange<br>237, 170, 2<br>D#9<br>Pale Blue<br>179, 225, 224<br>D#14<br>Pale Pink<br>227, 210, 182 | D#5<br>Purple<br>219, 117, 137<br>D#10<br>Dark Blue<br>3, 22, 213 |
| | | | Group B | | |
| Acetic Acid | D#15<br>Pale Brown<br>252, 247, 219 | | | | |
| Indole | D#16<br>Pale Purple<br>224, 134, 184 | | | | |
| Thiol Compound | D#17<br>Pale Cream<br>252, 254, 241 | | | | |
| Hydrogen sulfide | D#18<br>Pale Brown<br>199, 175, 139 | | | | |
| Ethanol | D#19<br>Dijon<br>142, 132, 90 | | | | |
| | | | Group C | | |
| Tris buffer | D#20<br>Pale Pink<br>212, 175, 140 | D#21<br>Pale Purple<br>194, 182, 192 | D#22<br>Pink<br>245, 126, 132 | | |
| 1% epinephrine | D#20<br>Pale Green<br>169, 176, 107 | D#21<br>Pale Blue<br>225, 237, 223 | D#22<br>Pink<br>250, 124, 128 | | |
| 1% morpholine | D#20<br>Pale Pink<br>194, 170, 134 | D#21<br>Pale Blue<br>188, 199, 203 | D#22<br>Pink<br>248, 170, 162 | | |
| 10% trimethylamine | D#20<br>Pale Pink<br>204, 173, 130 | D#21<br>Pale Purple<br>198, 164, 181 | D#22<br>Pink<br>246, 133, 146 | | |

Overall, after a series of selection and optimization process, a total of 23 chromogenic assays, which cover a wide range of viable pathogen metabolic biomarkers, were selected and used for further study.

Figure 3:
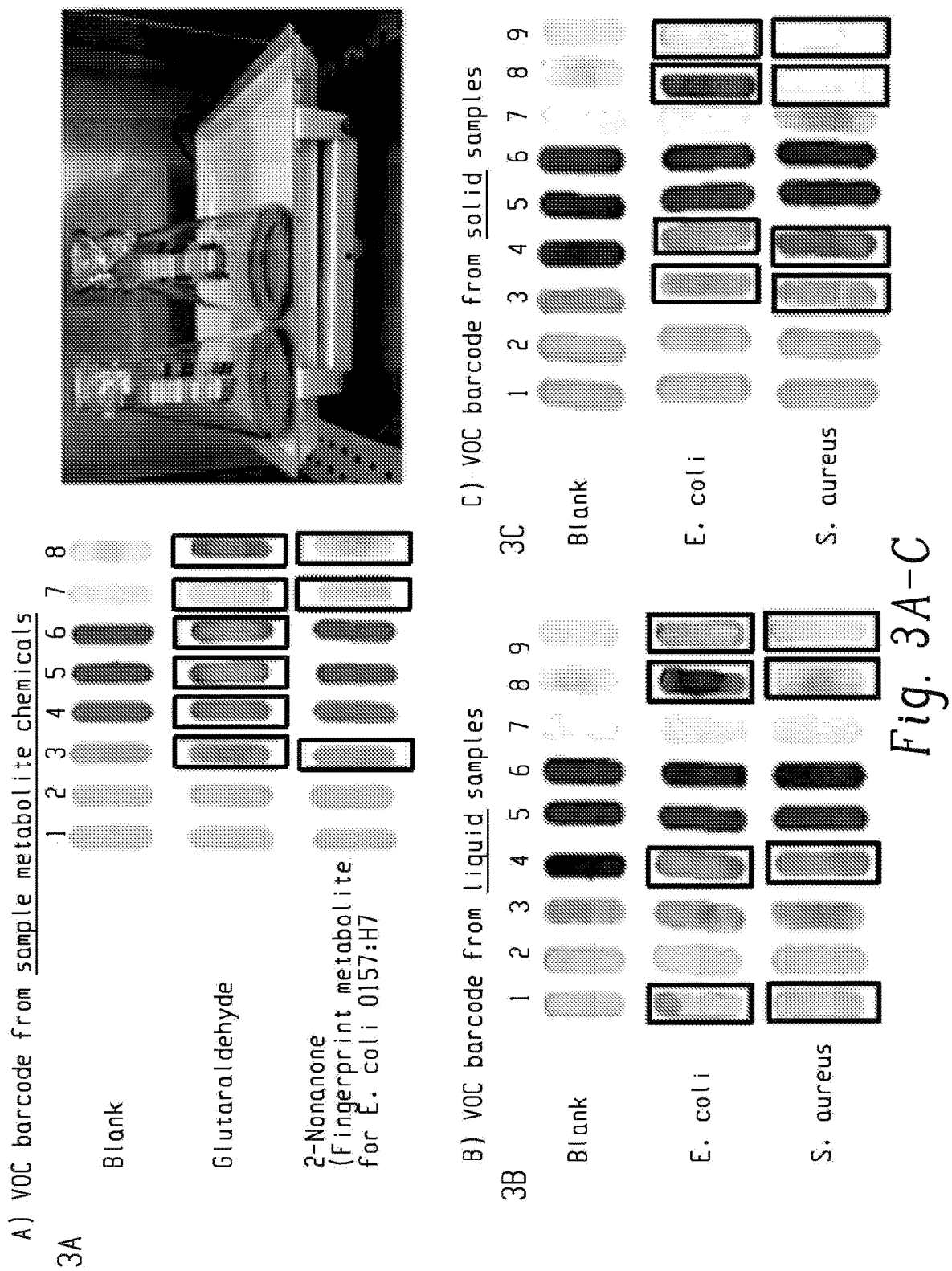
FIGS. 3A-C show selected array patterns from VOC testing of representative metabolite chemicals 3A) glutaraldehyde and 2-nonanone; 3B) liquid samples inoculated with *E. coli* and *S. aureus*; 3C) solid samples inoculated with *E. coli* and *S. aureus*. Each square indicates a specific dye reaction that provides discriminatory power between microbe-microbe or microbe-blank.

FIG. 3 shows further results with using CA with chromogenic nano-dyes. In FIG. 3(a), glutaraldehyde (representative acetaldehyde) and 2-nonanone (representative ketone and fingerprint metabolites of *E. coli* O157:H7) were used to demonstrate the chromogenic response of CA. FIG. 3(a) showed that amine-containing nano-dyes generates distinctive color changes when in contact with aldehyde and ketone volatile organic compounds. The color change is due to nucleophilic addition of carbonyl group by an amine in the formation of an imine, which gives a difference UV-vis absorption band. The addition of aldehyde reduced silver ions in Tollen's reagent and copper ions in Benedict's reagent on a test strip. Indole also formed a red complex with p-dimethylaminobenzaldehyde in Kovac's reagent drop casted on a test strip.

Example 2: Application of Preliminary Array Test Strips in Microbial Samples

CA assay was developed and validated on its capability to differentiate viable pathogen at high specificity and selectivity. CA color pattern was generated using single culture viable pathogens at various concentrations and growth conditions (including media, model food, temperature, pH, gas atmosphere, and simulated food processing and storage conditions).

The CA was used for microbial samples testing. All major foodborne pathogens, including non-typhoidal *Salmonella, Listeria monocytogenes, Campylobacter, Clostridium perfringens, Vibrio vulnificus, Shigella*, and STEC non-O157: H7 were included. The strains were revived from −80° C. by growing in BBL' BHI broth (Becton, Dickinson and Company, Sparks, MD) overnight to obtain standard microbial cultures and spreading on an agar petri dish (Difco™, Becton, Dickinson and Company, Sparks, MD) to provide single colonies. To determine volatile organic compound from liquid culture, aliquots of the overnight microbial culture were inoculated into an Erlenmeyer flask containing 30 mL BHI broth to adjust the starting microbial number to $10^3$ CFU/mL. The CA assemblies were mounted above the liquid surface and all flasks were incubated under 37° C. for 4 hours. Then the CA assemblies were retrieved after incubation and scanned to record the color changes. Similar approach was used when evaluating CA performance on solid media and in model food samples.

Figure 4:
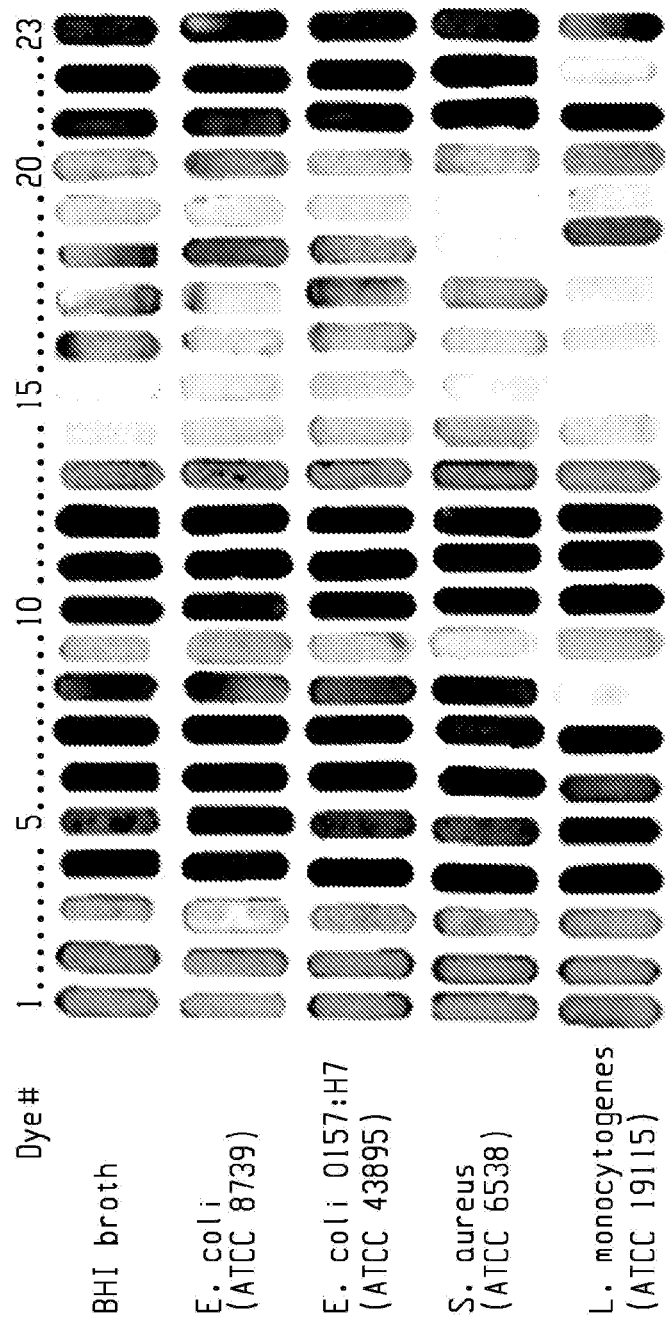
FIG. 4 shows CA patterns from VOC testing for sterile brain heart infusion (BHI) broth, *E. coli*, *E. coli* 0157: H7, *S. aureus* and *L. monocytogenes* grown in BHI broth at 37° C. for 12 hours.

In a specific experiment, *E. coli* (ATCC 8739), *E. coli* 0157: H7 (ATCC 43895), *S. aureus* (ATCC 6538) and *L. monocytogenes* (ATCC 19115) were selected as representative foodborne pathogens in BHI broth. The initial concentration was $10^2$ CFU/mL and incubated at 37° C. for 4 hours. All CA color patterns were scanned using HP Laserjet Pro M127fn scanner, with −10 brightness and 30 contrast settings, and 1200 dpi resolution. The scanned images were processed by MATLAB (R2018a, MathWorks, Inc., Natick, MA) to extract R/G/B color space, paired with respective microbial identity, quantity, media, time, and temperature. As shown in FIG. 4, the CA exhibited unique discriminatory power between different pathogens, even at a strain-level fidelity. The array pattern generated by *E. coli* and *E. coli* 0157: H7 showed visible color difference at strip #12, #15-18 (circled in FIG. 4). For *E. coli* and *S. aureus*, strip #12, #14-17 (circled in FIG. 4) showed visible color difference. For *L. monocytogenes*, #8 & 9, #12 and #15-18 showed visible color difference compare with other microbe. The CA color patterns generated by four microbes were all different from the control of sterile BHI broth. This demonstrates that the obtained color change pattern is directly related to viable pathogens presented in the BHI broth. The proof-of-concept results strongly shows that the integration of nano-dyes exhibits unparalleled power in differentiating microbe at stain level fidelity. It should be brought noted that $10^2$ CFU/mL inoculation and 4 hour incubation were only intended for preliminary experiment, and are unnecessary for practical applications in further stages.

Example 3: Sensitivity and Quantitative Modeling

Figure 5:
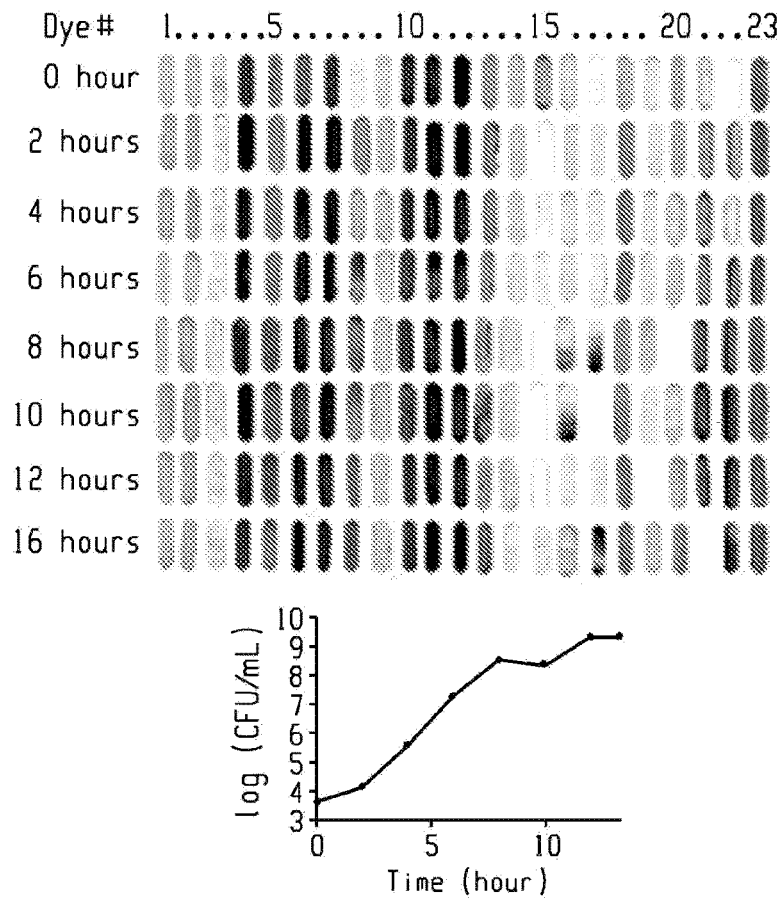
FIG. 5 top panel shows CA responses to *E. coli* (ATCC 8939) growth in BHI broth for 16 hours. Control indicates the CA pattern before the assay strip was mounted in the flask containing microbial culture.

To determine the CA sensitivity or limit of detection, the color patterns obtained at different microbial population were studied. An appropriate volume of overnight *E. coli* (ATCC 8939) culture was inoculated in an Erlenmeyer flask containing 30 mL BHI broth with the initial concentration at $10^3$ CFU/mL. The flask was incubated at 37° C. for 16 hours. CA color change patterns at different time points were retrieved and the microbial population was counted using a standard plate counting method. As shown in FIG. 5, the CA exhibited obvious color change over the 16-hour *E. coli* growth. The visible color change of CA pattern can be observed starting after 6 hours incubation. With the microbial population from FIG. 5, the minimal microbial population need to show visible color change is about $10^6$ CFU/mL. The color pattern was both time-dependent and concentration-dependent.

The CA color pattern was processed and modeled using machine learning algorithm to determine the quantitative relationship between color-codes and bacteria quantity. The algorithm also helped determining the limit of detection of the proposed CA method. In a typical multilayer neural network architecture, the CA color pattern will be the input, and the bacteria quantity and associated environment condition parameters will be the output. The network can be trained with respect to the training data sets under well-controlled conditions. The trained network can approximate a non-linear function via the network parameters to model the relationship between the color pattern and overall condition of the food sample.

Example 4: Temperature-Abuse and Continuous Monitoring

Viable pathogens are sensitive to environment, including temperature. All major foodborne pathogens can recover and grow rapidly and even exponentially at room temperature, even if they are only exposed at the warmer temperature for a few hours. Temperature abuse along the food supply chain or at the consumer home is one of the major malpractices that could lead to devastating effects on food safety. Therefore, the response of CA at different temperature was also evaluated.

Figure 6:
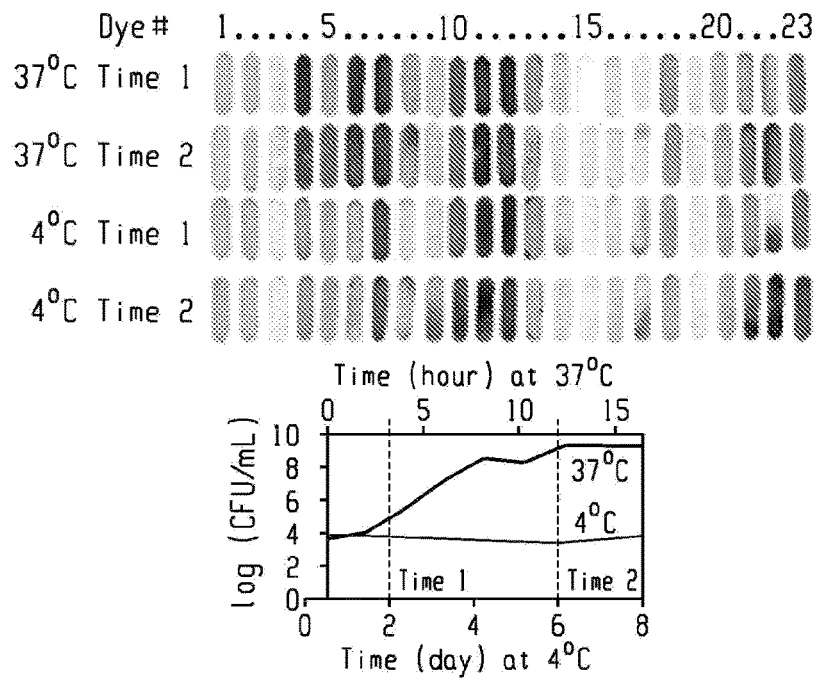
FIG. 6 top panel shows different CA patterns generated at 4° C. and 37° C. by *E. coli* in BHI broth. The initial concentration was $10^3$ CFU/mL.

As it showed in FIG. 6, similar to 37° C. incubation, CA showed different color change pattern for the four strains under refrigerated incubation. It should be noted that the CA pattern at 4° C. incubation is distinctively different than the pattern at 37° C. incubation. This could be attributed to different pathogen metabolism at different temperature settings, and the cellular mechanisms to cope with cold shock at refrigeration temperature. Specifically, *E. coli* secreted a greater amount of aldehydes/ketones generation at 37° C. This preliminary result strongly indicates CA's capability to differentiate sample maintained at refrigeration from compromised sample with temperature abuse.

In addition, one remarkable discovery from the preliminary experiments was that CA was able to sense volatile organic compound from very low loading of viable microbe ($10$-$10^3$ CFU/mL) at refrigeration conditions. These results showed that the CA can be used for 1) continuous monitoring of food hygiene status; 2) differentiate different temperatures; 3) capture temperature abuse history.

Example 5: On-Demand Sampling

CA can be also deployed on-demand, like a pH test strip. For on-demand sampling, freshly assembled CA was stored in a seal container to minimized influences from oxygen and environmental volatile organic compounds. Upon sampling, CA was removed from the storage container and exposed to samples with volatile organic compound for 15-30 min to obtain color change. The color change patterns were then further analyzed using machine learning algorithm to reveal the overall condition of the food. Such application of the CA include food that are in both pre-harvest and post-harvest stages. In pre-harvest stage, CA provides valuable information to the growers, farmers, brewers, fishermen, regarding the overall status of food to avoid injuries, diseases, or wastes. In post-harvest application, CA provides valuable information to the packers, processors, distributors, storage facilities, retail facilities, regulators, and consumers regarding the quality and safety status of food or processed food.

Example 6: Multiplex Quantification by Machine Learning and Sensor Fusion

Each food commodity often faces multiple, and sometimes random, threats from dozens of major infectious microbes. Multiplex quantification of major pathogens in real food is thus an important feature of the assays described herein. Both single culture and dual-strain cocktails can be used in creating the CA database. $10^2$ CFU/mL of the single and dual-strain cocktail (15 combinations) will be used as the starting population for each strain. CA assemblies will be mounted in these dual strain cocktails and the CA color change patterns are recorded to construct a machine learning database and algorithm. Standard media, including BHI (for viable but non-culturable microbes) and TSA will be used. Model food will be used. Temperature variations will include 4, 12, 24, and 37° C.

Example 7: Algorithm Development for Machine Learning and Sensor Fusion

We trained a neural network to identify and quantify pathogens. For example, for each of the array test strip, we will pre-process the strip to generate a triplet (Red, Green, Blue/RGB) in color space. The input of the multilayer neural network will be the all the triplets associated with the array, as well as the growth conditions. The output will be the pathogen identity and quantity. The multilayer neural network architecture will be optimized with respect to the training datasets. The automatic image processing will significantly reduce the amount of labor and training involved to complete assay, and thus enables end-user applications, including routine industry QA/QC and consumer point-of-care testing.

Figure 7:
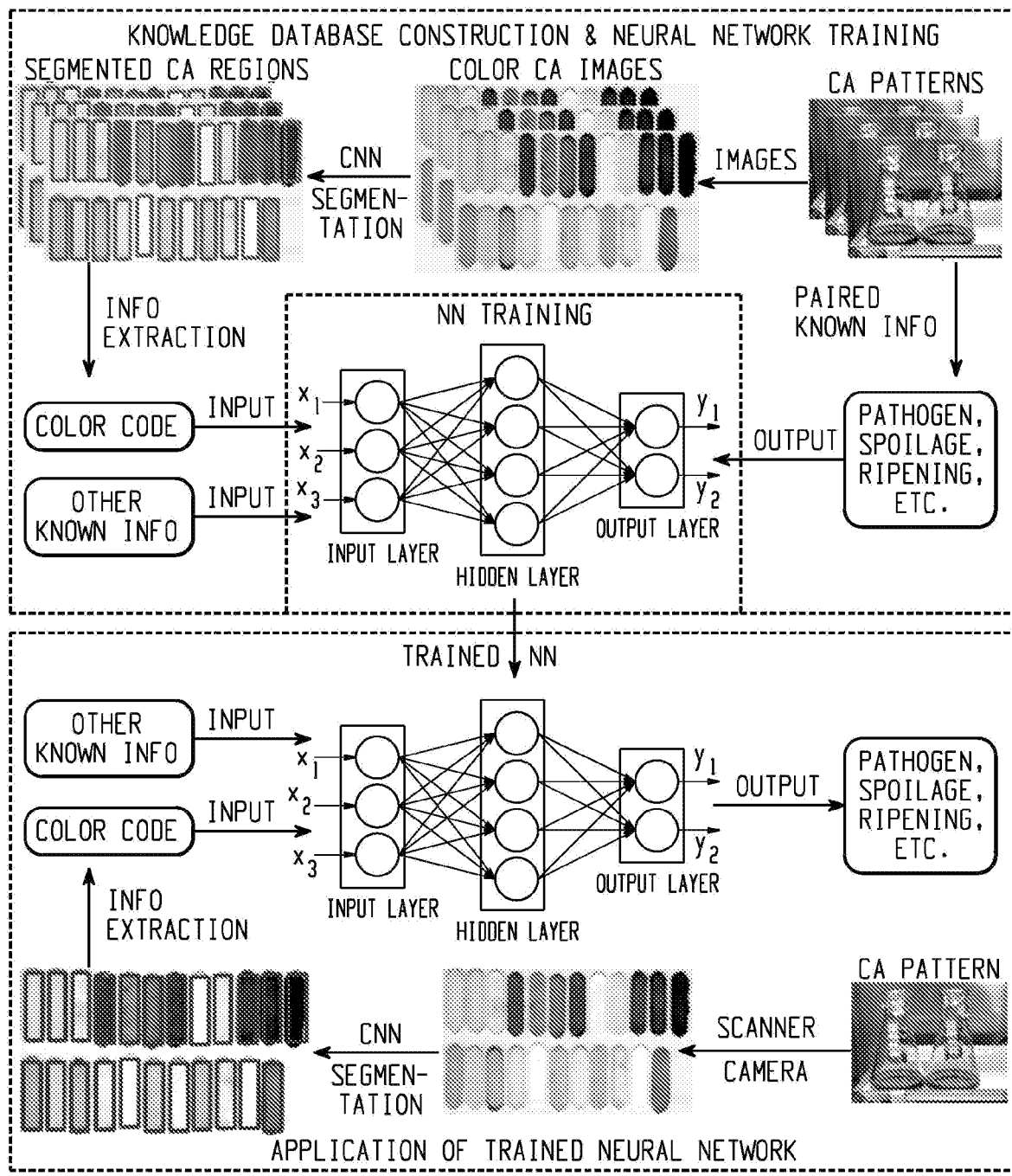
FIG. 7 shows database construction and multi-layer CNN training. Flowchart indicates deep learning technique for decoding the information of bacterial identity and quantity from the CA patterns. Top panel: database construction and algorithm training; Bottom panel: application of the trained CNN for unknown identification.

FIG. 7 shows the database construction and multi-layer CNN training. Flowchart indicates deep learning techniques are employed to automatically segment the strips and extract the triplets for decoding the information of bacterial identity and quantity from the CA patterns. Examples of deep learning techniques includes but not limited to conventional neural network (CNN), fully convolutional network (FCN), feature pyramid network (FPN), generative adversarial network (GAN), deep convolutional network (DCN), DeepLab, etc. Top: database construction and algorithm training; Bottom: application of the trained CNN for unknown identification.

Example 8: Validation and Unknown Testing in Model Food

One key to a successful deployment of a CA in the food supply chain is the functionality and applicability in real food, especially when food emits shifting backgrounds of volatile organic compound. Therefore, in this fresh produce, climacteric produce, meat, poultry, and seafood are selected as the model foods to validate the CA method and machine learning algorithm. Romaine lettuce is used as a model for fresh produce. Sirloin steak and chicken breasts are selected as representative meat and poultry models, respectively. Tuna and raw oysters are used as seafood models, according to the 2015 CDC report about outbreak food types. Exemplary single or cocktail microbial cultures and different ripening status in each sample food are shown in Table 4.

TABLE 4

| Food samples with single or multiplex microbial cultures, and different ripening status. | | |
|---|---|---|
| Fresh produce (FP) samples - Multiple Pathogens (FIG. 8) | Seafood (S) samples - Mixture of Spoilage and Pathogen (FIG. 9) | Climacteric Produce (CP) sample - Ripening Conditions (FIG. 10) |
| FP1: *E. coli* O157:H7 <br> FP2: *Listeria monocytogenes* <br> FP3: *E. coli* O157:H7 + *Listeria monocytogenes* | S1: *Shewanella putrefaciens* <br> S2: *Morganella morganii*. <br> S3: *Shewanella putrefaciens* + *Morganella morganii* | CP1: Fully Ripe <br><br> CP2: Underripe |

Figure 8:
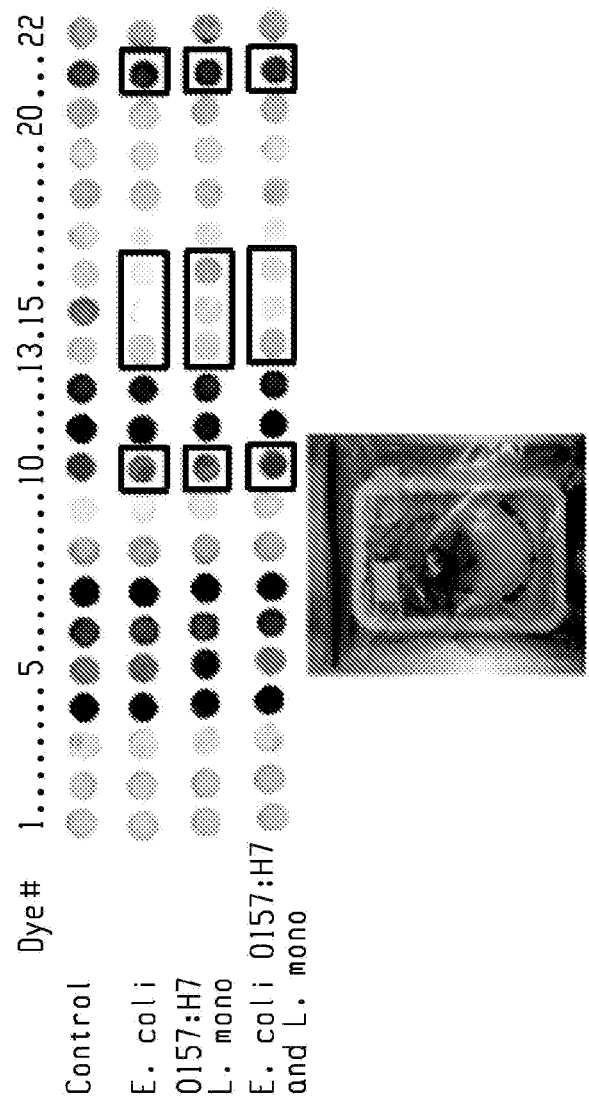
FIG. 8 shows multiplex identification of viable pathogen by CA in fresh-cut Romaine lettuce in simulated temperature abuse scenarios (12° C. for 7 days). From top to bottom: CA exposed to fresh-cut Romaine lettuce with no pathogens inoculated; with *E. coli* O157:H7 only; with *L. monocytogenes* serotype ½b only; with both *E. coli* O157:H7 and *L. monocytogenes* serotype ½b.

FIG. 8 shows multiplex identification of viable pathogen by CA in fresh-cut Romaine lettuce in simulated temperature abuse scenarios (12° C. for 7 days). From top to bottom: CA exposed to fresh-cut Romaine lettuce with no pathogens inoculated; with *E. coli* O157:H7 only; with *L. monocytogenes* serotype ½b only; with both *E. coli* O157:H7 and *L. monocytogenes* serotype ½b.

For instance, single and cocktail cultures of pathogens are added to 250 g of fresh or fresh-cut Romaine lettuce heart with a starting concentration of $10^2$ CFU/g. The inoculated lettuce is incubated at 37° C. for up to 24 hours and 4° C. for up to 10 days. After incubation, 10 g of food sample is homogenized in 90 ml sterilized peptone water using a blender (Stomacher® 400 Biomaster) for 3 minutes. The CA pattern is pictured and analyzed. For other food samples, food samples (60 g) are inoculated with $10^2$ CFU/g pathogens and then incubated at 24° C. for up to 24 hours and 4° C. for up to 10 days. The inoculated lettuce is incubated at 24° C. for up to 16 hours and 4° C. for up to 8 days. All CA are mounted in the commercial container or package for these food samples to allow the sensing of volatile organic compound.

Example 9: Capturing Temperature Abuse History in Packaged Products

With the establishment of the relation between pathogen population and CA color change, CA s ca be further validated in packaged fresh produce in the state-of-art BSL-2+ supermarket at USDA-ARS. Fresh Romaine lettuce is used as model food and purchased from a local produce wholesale market in Jessup, MD The pathogen inoculation and storage conditions simulate real-world scenarios. Briefly, a cutter will be artificially contaminated with approximately 5×10⁵ pathogen cells. 100 pounds of lettuce was then cut with the contaminated cutting blade. The contaminated blade will be used to introduce cross-contamination on fresh-cut lettuce.

To determine the initial microbial concentration on the fresh-cut lettuce, immediately after cutting, samples will be homogenized in a blender (Stomacher® 400 Biomaster) with 150 ml PBS (Seward Limited, London, England) for 2 min at 230 RPM. Homogenates are filtered through sterile filter stomach bags. Duplicate samples will be plated onto LB agar plates using a Wasp II Spiral Plater (DW Scientific, West Yorkshire, England). The microbial colonies were incubated for enumeration.

For storage test, the pathogen contaminated samples will be bagged in air permeable bags, with CA assemblies mounted in the bag and then transferred to a 12-foot long (3.66 m) retail display case in the USDA-ARS supermarket. The case included standard LED light, air curtains, and the display case duty operations were regulated by a digital thermostat set at 4° C.

For temperature abuse validation, lettuce spiked with pathogens were continuous monitored by the CA. The spiked lettuce was stored at 4° C. for 0, 1, 2, 3, 4 and 5 days. The samples are then brought to 24° C. for 0 (control), 2, 4, 6, 8 hours, followed by refrigeration for another 2 days. The CA color pattern can be continuously recorded for analysis. Based on our preliminary results, samples exposed to room temperature are expected to leave a permanent pattern change to provide the unique capability in sensing, recording and visually displaying temperature abuse history, which are one of the major malpractices that causes outbreaks and foodborne illnesses. The proposed strategy has many food safety applications, including spoilage and pathogen monitoring, risk assessment, smart packaging, QA/QC, and consumer POC testing.

Example 10: Preliminary Data on CA Machine Learning Algorithm

Existing paper sensors have two drawbacks, among others. The first limitation is subjectivity or testing inaccuracy due to the limit of human vision (if read by a human). The second limitation is the presence of interfering background noises under commercial settings. Since volatile organic compounds generated by various non-targeted and changing background of microorganism and food matrices, this can significantly confound the detection of targeting volatile organic compounds from targets and render the test inaccuracy. Thus, included herein is the development and integration of an advanced machine learning algorithm with the CA. The images of each CA pattern may be captured via a camera or a scanner. The images may be digitized with the tri-stimulus features (RGB or LAB values) extracted (FIG. 7). Advanced deep learning techniques including program codes developed by the inventors may be used to train a multilayer neural network. The input of our multilayer neural network also may include all other variables such as the physiological status of food, plant defects, injuries and diseases, microbial identity, microbial quantity, as well as temperature abuse that are associated with each CA pattern.

All input datasets used in the training and improve the accuracy of the multilayer neural network. For example, a CA pattern generated from a real food sample is analyzed using the neural network to reveal the overall condition of the food, including, the physiological status of food, plant defects, injuries and diseases, microbial identity, microbial quantity, as well as temperature abuse history. In addition, an automatic pattern recognition system or app based on cell phones or digital cameras will be developed. The automatic image processing will a) significantly reduce the amount of labor and training involved to complete the assay, b) minimize false-positive and false-negative results, c) enable end-user applications, including routine industry QA/QC and consumer point-of-care testing, and d) optimize and improve the accuracy of the multilayer neural network architecture over time and number of uses, with respect to the accumulation of larger datasets from users, who use the CA and provide data feedback to the neural network datasets.

Figure 11:
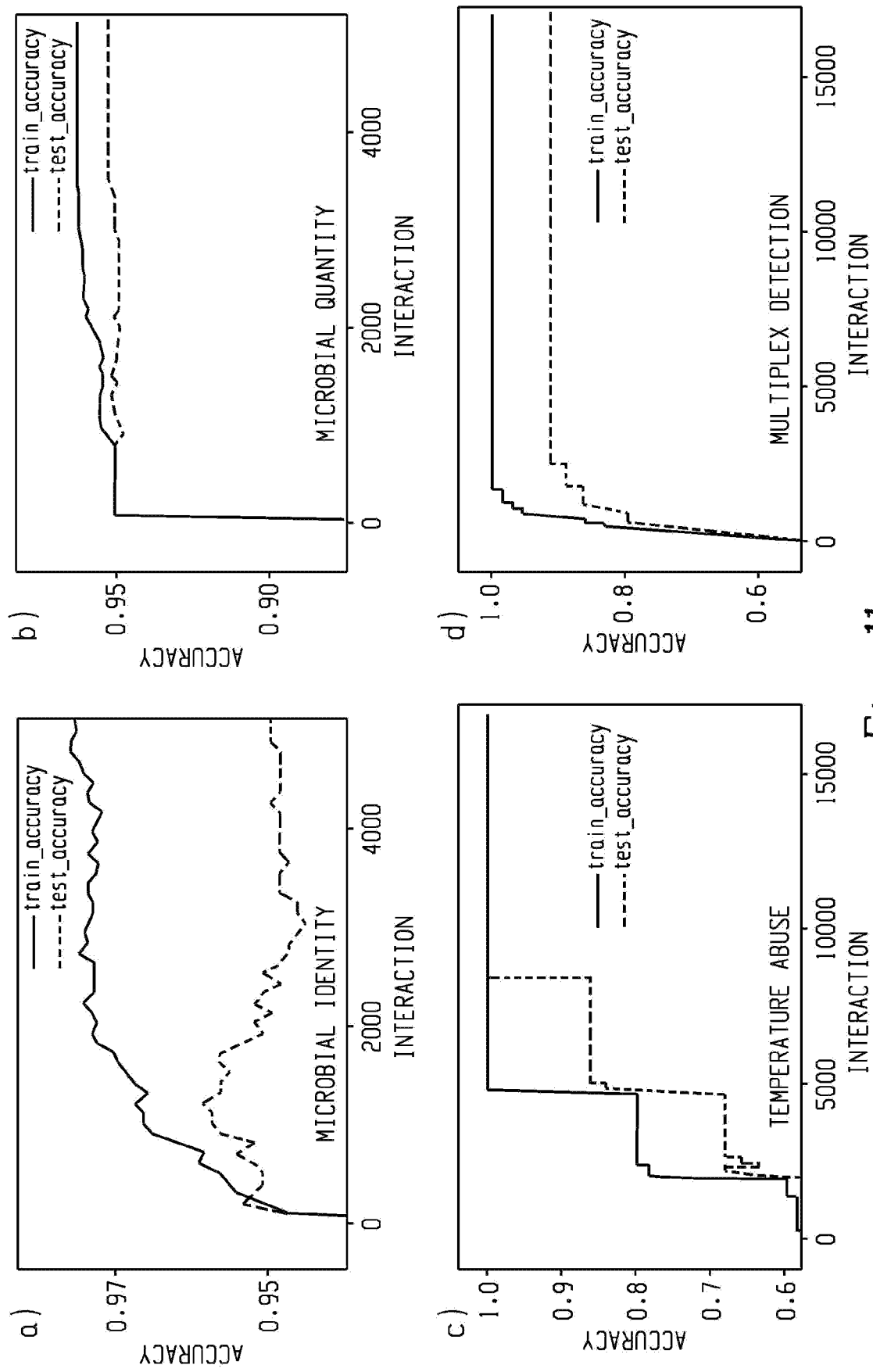

As shown in FIG. 7, a multilayer neural network was successfully trained using a preliminary set of CA patterns (with 23 nano-dyes). A sample with *E. coli* was selected as an unknown sample to test the trained neural network. The identity and quantity of *E. coli* in the unknown sample was confirmed by the trained neural network, and the results were validated from the conventional plate count method on selective agar. FIG. 11 shows machine learning of CA pattern using trained NN. Red line indicates training accuracy using 75% of the CA replicates. Blue line indicates test accuracy, which was validated using the remaining 25% of the PCA replicates that were unknown to the NN during training. a) Identification of microbial contaminant (CA data from single culture in BHI); b) Quantification of microbial contaminant (CA data from single culture in BHI); c) Detecting temperature abuse (CA data from single culture in BHI); d) Multiplex identification of microbial contaminants (CA data from both single and cocktail cultures in fresh-cut romaine lettuce). The accuracy of the prediction can be defined as:

$$\text{Accuracy} = \text{Samples rightly predicted}/\text{Total samples tested}$$

The accuracy of identifying microbial stain was over 95% (FIG. 11). The accuracy of quantifying viable microorganisms in the sample was over 95% (FIG. 11). The accuracy of capturing temperature abuse events was at a 100% accuracy rate (FIG. 11). More important, the CA-machine learning model was able to achieve 91% accuracy in complex samples with multiplex signals (FIG. 11), such as coexistence of different pathogens, pathogens and spoilage-causing microorganisms, and physiological changes of food due to ripening. The results strongly indicate the potential of machine learning and sensor fusion in automated pattern recognition to extrapolate microbial identity and quantity from CA patterns. The accuracy and variation loss of automated pattern recognition can improve with a growing sample size, which is the key advantage of the deep learning technique. Therefore, it is anticipated that the trained neural network will deliver substantially higher accuracy and lower variation loss over time and number of uses.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A chromogenic assay, comprising
a substrate comprising an array of 10 or more dyes which react with volatile organic compounds, wherein each of the dyes of the array of 10 or more dyes are chromogenic when reacted with volatile organic chemical (VOC) biomarkers, wherein the VOC biomarkers comprise acids, alcohols, aldehydes, alkenes, amines, antioxidants, aromatic compounds, esters, ethylene, lactones, ketones, organosulfur compounds, sulfides, reactive oxygen species, terpenes, or a combination thereof; wherein the array of 10 or more dyes comprises 2,4-dinitrophenylhydrazine (phenylhydrazine), 4,4'-azodianiline (dianiline) and pararosaniline (fuchsine), bromophenol blue, nitrazine yellow, chlorophenol red, Tollen's reagent, Benedict's reagent, zinc nitrate, and sodium nitroprusside.

2. The chromogenic assay of claim 1, wherein the array of 10 or more dyes provides an array of color change upon exposure to VOC biomarkers from viable pathogens, microorganisms, fresh produce, climacteric produce, raw or processed meat, raw or processed poultry, raw or processed seafood, spices, dairy, grain, eggs, alcoholic or non-alcoholic beverages, other processed and packaged food, or a combination thereof.

3. The chromogenic assay of claim 1, wherein each of the dyes of the array of 10 or more dyes is infused in a porous adsorbent, a butyl acrylate polymer nanoparticle, or an anion exchange bead.

4. The chromogenic assay of claim 1, wherein the chromogenic assay can detect viable microorganisms at a concentration of 10-1,000,000,000 colony forming unit per milliliter or of 10-1,000,000,000 colony forming unit per gram.

5. A method of detecting volatile organic chemical (VOC) biomarkers, comprising
contacting the chromogenic assay of claim 1 with a sample or sample headspace, wherein the sample or sample headspace is suspected of containing VOC biomarkers, and detecting, based on a colorimetric pattern on the chromogenic assay after contacting, the VOC biomarkers.

6. The method of claim 5, wherein the chromogenic assay is an on-demand sampling assay.

7. The method of claim 5, wherein the sample is a food sample, and a source of the volatile organic chemical biomarkers is identified as a microorganism.

8. The method of claim 7, wherein the microorganism comprises *Aspergillus* spp., *Bacillus* spp., *Campylobacter* spp., *Clostridium* spp., *Cronobacter sakazaki, Cryptosporidium* spp., *Cyclospora cayetanensis, Giardia intestinalis, Listeria monocytogenes, Morganella morganii, Mycobacterium bovis*, pathogenic *E. coli* spp., *Salmonella* spp. (*S. enterica* serotype *Typhi* and non-typhoidal), *Shigella* spp., *Staphylococcus aureus, Streptococcus* spp., *Trichinella* spp., *Toxoplasma gondii, Vibrio* spp., *Yersinia* spp., *Acetobacter* spp., Asinetobacter spp., *Aeromonas* spp., *Bacillus* spp., *Botrytis cinerea*, Brochothrix spp., *Candida* spp., *Carnobacterium* spp., *Cladosporium* spp., *Claviceps* spp., *Enterobacter* spp., *Enterococcus* spp., *Erwinia carotovora, Fusarium* spp., generic *E. coli* spp., *Geotrichum* spp., *Gluconobacter* spp., Klebisella spp., *Lactobacillus* spp., *Leuconostoc* spp., *Moraxella* spp., *Mucor* spp., Pedicoccus spp., *Penicillium* spp., *Photobacterium* spp., *Proteus* spp., *Pseudomonas* spp., *Psychrobacter* spp., *Rhizopus* spp., *Saccharomyces* spp., *Serratia* spp., *Shewanella* spp., *Sportrichum* spp., *Yersinia* spp., *Acetobacter* spp., *Bifidobacterium* spp., *Candida* spp., *Enterococcus* spp., *Geotrichum* spp., *Gluconobacter* spp., lactic-acid bacteria (LAB), *Lactobacillus* spp., *Lactococcus* spp., *Leuconostoc* spp., *Oenococcus* spp., *Pediococcus* spp., *Penicillium* spp., *Propionibacterium* spp., *Saccharomyces* spp., *Streptococcus* spp., *Weissella* spp.; or a combination thereof.

9. The method of claim 5, wherein a source of the volatile organic chemical (VOC) biomarkers is a pathogen on an edible plant, a livestock animal, or poultry.

10. The method of claim 5, wherein the sample is a food sample suspected of temperature abuse, and a source of the VOC biomarkers is identified as a microorganism.

11. The method of claim 10, wherein the microorganism comprises *Aspergillus* spp., *Bacillus* spp., *Brucella* spp., *Campylobacter* spp., *Clostridium* spp., *Cronobacter sakazaki, Cryptosporidium* spp., *Cyclospora cayetanensis, Giardia intestinalis, Listeria monocytogenes, Morganella morganii, Mycobacterium bovis*, pathogenic *E. coli* spp., *Salmonella* spp. (*S. enterica* serotype *Typhi* and non-typhoidal), *Shigella* spp., *Staphylococcus aureus, Streptococcus* spp., *Trichinella* spp., *Toxoplasma gondii, Vibrio* spp., *Yersinia* spp., *Acetobacter* spp., *Acinetobacter* spp., *Aeromonas* spp., *Bacillus* spp., *Botrytis cinerea*, Brochothrix spp., *Candida* spp., *Carnobacterium* spp., *Cladosporium* spp., *Claviceps* spp., *Enterobacter* spp., *Enterococcus* spp., *Erwinia carotovora, Fusarium* spp., generic *E. coli* spp., *Geotrichum* spp., *Gluconobacter* spp., Klebisella spp., *Lactobacillus* spp., *Leuconostoc* spp., *Moraxella* spp., *Mucor* spp., Pedicoccus spp., *Penicillium* spp., *Photobacterium* spp., *Proteus* spp., *Pseudomonas* spp., *Psychrobacter* spp., *Rhizopus* spp., *Saccharomyces* spp., *Serratia* spp., *Shewanella* spp., *Sportrichum* spp., *Yersinia* spp., *Acetobacter* spp., *Bifidobacterium* spp., *Candida* spp., *Enterococcus* spp., *Geotrichum* spp., *Gluconobacter* spp., lactic-acid bacteria (LAB), *Lactobacillus* spp., *Lactococcus* spp., *Leuconostoc* spp., *Oenococcus* spp., *Pediococcus* spp., *Penicillium* spp., *Propionibacterium* spp., *Saccharomyces* spp., *Streptococcus* spp., *Weissella* spp., or a combination thereof.

12. The method of claim 5, wherein the sample is a fresh food sample and a source of the VOC biomarkers is a species, genetic traits, physiological state, abnormal metabolism, ripeness, authenticity, and probiotic status of the food sample.

13. The method of claim 5, wherein contacting the chromogenic assay with the sample or sample headspace is continuous to monitor sample status, differentiation of temperature, or determination of temperature abuse history.

14. The method of claim 5, wherein contacting the chromogenic assay with the sample or sample headspace is continuous to monitor probiotic status of fermented food selected from yogurt, sauerkraut, kimchi, kefir, miso, tempeh, buttermilk, chocolate, cheese, cider, pickle, and sourdough.

15. The method of claim 5, wherein the sample comprises a fermented and/or aged food or beverage selected chocolate, cheese, balsamic vinegar, beer, and wine, and the method further comprises authenticity verification of the sample based on detection of the VOC biomarkers.

16. The method of claim 5, wherein the sample is a food sample selected from fresh produce, climacteric produce, raw or processed meat, raw or processed poultry, raw or processed seafood, spices, dairy, grain, alcoholic or non-alcoholic beverages, fermented food, and other processed and packaged food.

17. The method of claim 5, wherein the method is a method of detecting volatile organic chemical biomarkers for spoilage and pathogen monitoring, probiotic monitoring, authenticity testing, risk assessment, quality assurance/quality control (QA/QC), and consumer point-of-care (POC) testing.

18. An article comprising the chromogenic assay of claim 1, wherein the article is a sticker, a label, a standalone strip, a package, or a container.

* * * * *